(12) United States Patent
Burke et al.

(10) Patent No.: US 11,559,384 B2
(45) Date of Patent: Jan. 24, 2023

(54) STENT WITH SELECTIVELY CURVED REGION

(71) Applicant: BOSTON SCIENTIFIC SCIMED, INC., Maple Grove, MN (US)

(72) Inventors: Martin Burke, Galway (IE); Gerard Duignan, Roscommon (IE); Daniel Tuck, Galway (IE); Martyn G. Folan, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 614 days.

(21) Appl. No.: 16/431,128

(22) Filed: Jun. 4, 2019

(65) Prior Publication Data
US 2019/0365521 A1 Dec. 5, 2019

Related U.S. Application Data

(60) Provisional application No. 62/680,731, filed on Jun. 5, 2018.

(51) Int. Cl.
*A61F 2/04* (2013.01)
*A61B 17/11* (2006.01)
*A61F 5/00* (2006.01)
*A61M 25/01* (2006.01)

(52) U.S. Cl.
CPC .......... *A61F 2/04* (2013.01); *A61B 17/1114* (2013.01); *A61F 5/0083* (2013.01); *A61B 2017/1132* (2013.01); *A61F 2002/045* (2013.01); *A61M 25/0147* (2013.01)

(58) Field of Classification Search
CPC ........... A61F 2/07; A61F 2220/0075; A61F 2002/9511; A61F 2002/045; A61F 2/2439; A61F 2/954; A61F 2002/077; A61F 2002/9534
See application file for complete search history.

(56) References Cited

U.S. PATENT DOCUMENTS

| 5,035,706 A | 7/1991 | Giantureo et al. |
| 5,957,974 A * | 9/1999 | Thompson ................ A61F 2/90 |
| | | 623/1.13 |
| 5,984,957 A | 11/1999 | Laptewicz, Jr. et al. |

(Continued)

FOREIGN PATENT DOCUMENTS

| EP | 0897699 A2 | 2/1999 |
| EP | 1177779 A2 | 2/2002 |

(Continued)

OTHER PUBLICATIONS

International Search Report and Written Opinion dated Sep. 6, 2019 for International Application No. PCT/US2019/035385.

*Primary Examiner* — Brian E Pellegrino
(74) *Attorney, Agent, or Firm* — Seager, Tufte & Wickhem, LLP

(57) ABSTRACT

A stent with a selectively curved region. The stent includes a radially expandable tubular framework and a covering surrounding the tubular framework. A stent also includes a drawstring having a first end attached to the tubular framework at a first attachment location proximate the distal end of the tubular framework. The second end of the first drawstring is manipulatable proximate the proximal end of the tubular framework to deflect the tubular framework into a curved configuration.

18 Claims, 32 Drawing Sheets

(56) References Cited

U.S. PATENT DOCUMENTS

| | | |
|---|---|---|
| 6,792,979 B2 | 9/2004 | Konya et al. |
| 6,974,471 B2 | 12/2005 | Van Schie et al. |
| 7,252,680 B2 | 8/2007 | Freitag |
| 7,976,575 B2 | 7/2011 | Hartley |
| 7,998,189 B2 | 8/2011 | Klbel et al. |
| 8,021,421 B2 * | 9/2011 | Fogarty ............... A61F 2/2409 623/2.38 |
| 8,043,356 B2 | 10/2011 | Klbel et al. |
| 8,414,635 B2 | 4/2013 | Hyodoh et al. |
| 8,663,309 B2 | 3/2014 | Chobotov |
| 8,876,880 B2 | 11/2014 | Hyodoh et al. |
| 8,945,205 B2 | 2/2015 | Greenberg |
| 9,237,960 B2 | 1/2016 | Rasmussen et al. |
| 9,375,308 B2 | 6/2016 | Norris |
| 9,662,196 B2 | 5/2017 | Roeder et al. |
| 9,770,322 B2 | 9/2017 | Burkart et al. |
| 9,782,282 B2 | 10/2017 | Bloss et al. |
| 9,877,858 B2 | 1/2018 | Beard et al. |
| 9,907,684 B2 | 3/2018 | Connor et al. |
| 2002/0007208 A1 | 1/2002 | Strecker |
| 2003/0088305 A1 | 5/2003 | Van Schie et al. |
| 2005/0049674 A1 | 3/2005 | Wang et al. |
| 2008/0114440 A1 | 5/2008 | Hlavka et al. |
| 2009/0099640 A1 | 4/2009 | Weng |
| 2010/0256728 A1 * | 10/2010 | Rea Peterson ............ A61F 2/07 623/1.13 |
| 2013/0041456 A1 | 2/2013 | Greenberg |
| 2013/0289713 A1 * | 10/2013 | Pearson .................. A61F 2/954 623/1.35 |
| 2014/0316518 A1 * | 10/2014 | Kheradvar ............ A61F 2/2439 623/2.11 |
| 2014/0350694 A1 * | 11/2014 | Behan ...................... A61F 2/04 623/23.65 |

FOREIGN PATENT DOCUMENTS

| | | | |
|---|---|---|---|
| EP | 1738793 A1 | 1/2007 | |
| EP | 1870057 A1 | 12/2007 | |
| WO | 200303948 A1 | 5/2003 | |
| WO | 2004045450 A2 | 6/2004 | |
| WO | 2009126227 A2 | 10/2009 | |
| WO | WO-2017192710 A1 * | 11/2017 | ............... A61F 2/82 |

* cited by examiner

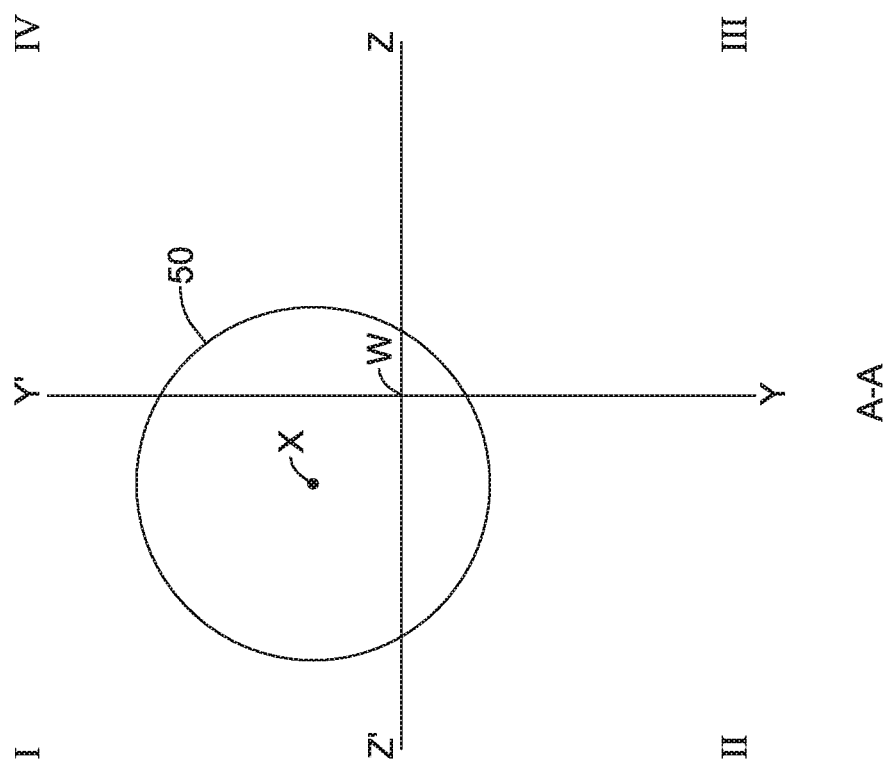

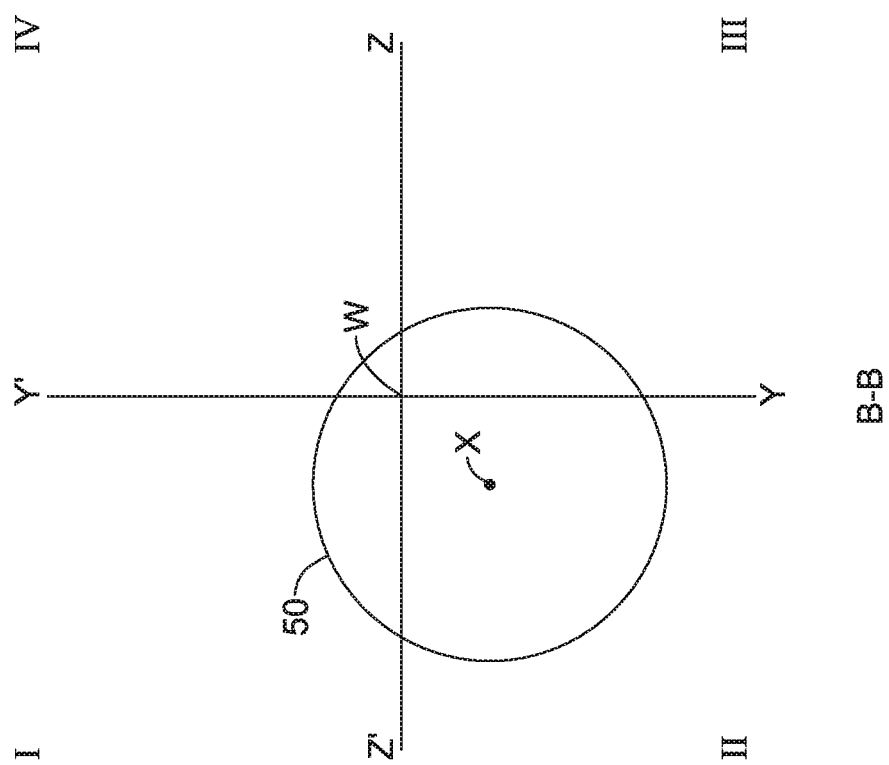

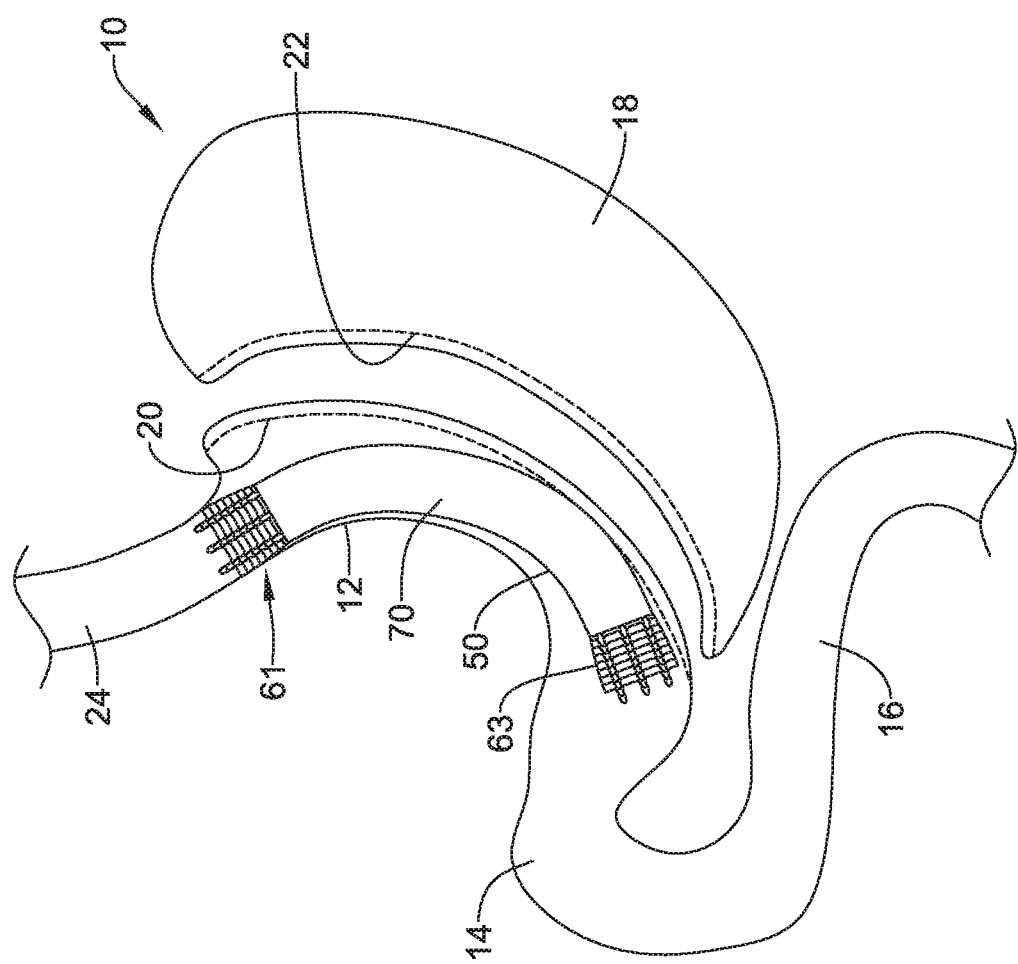

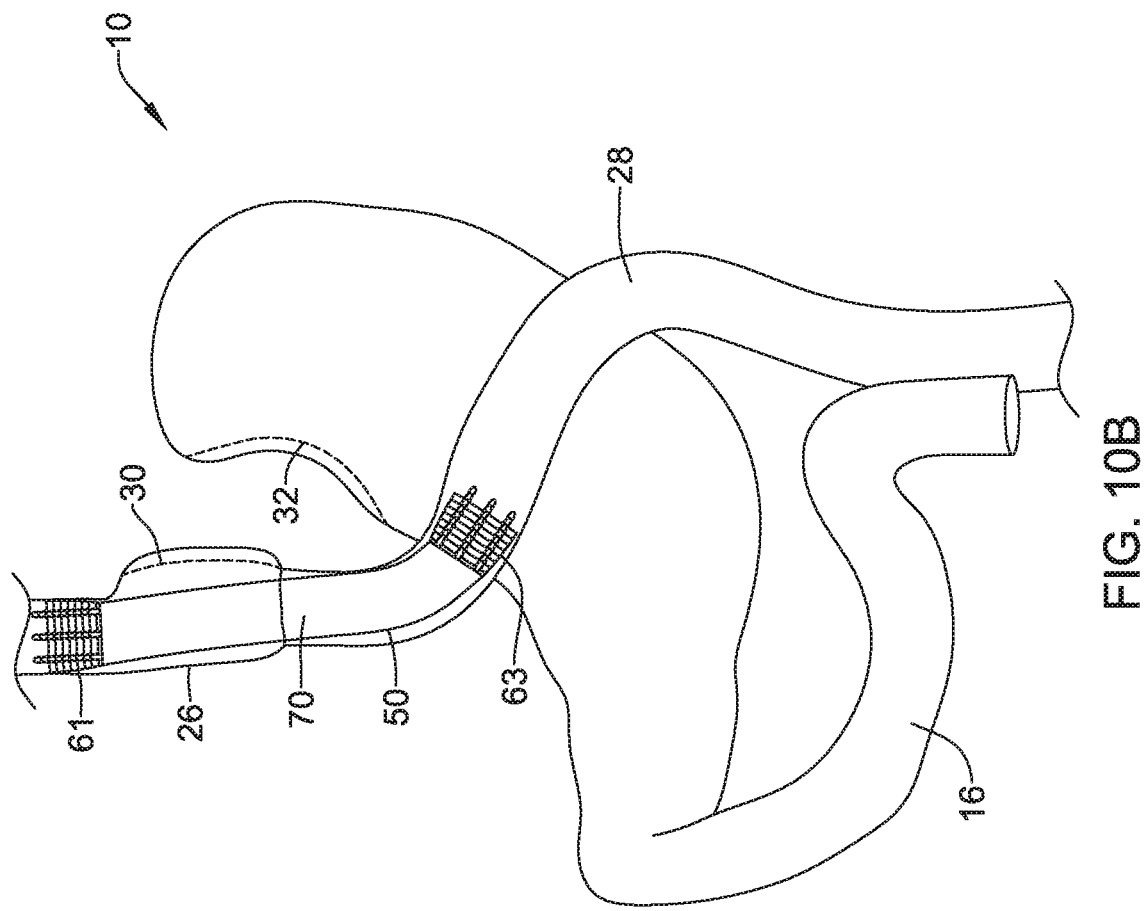

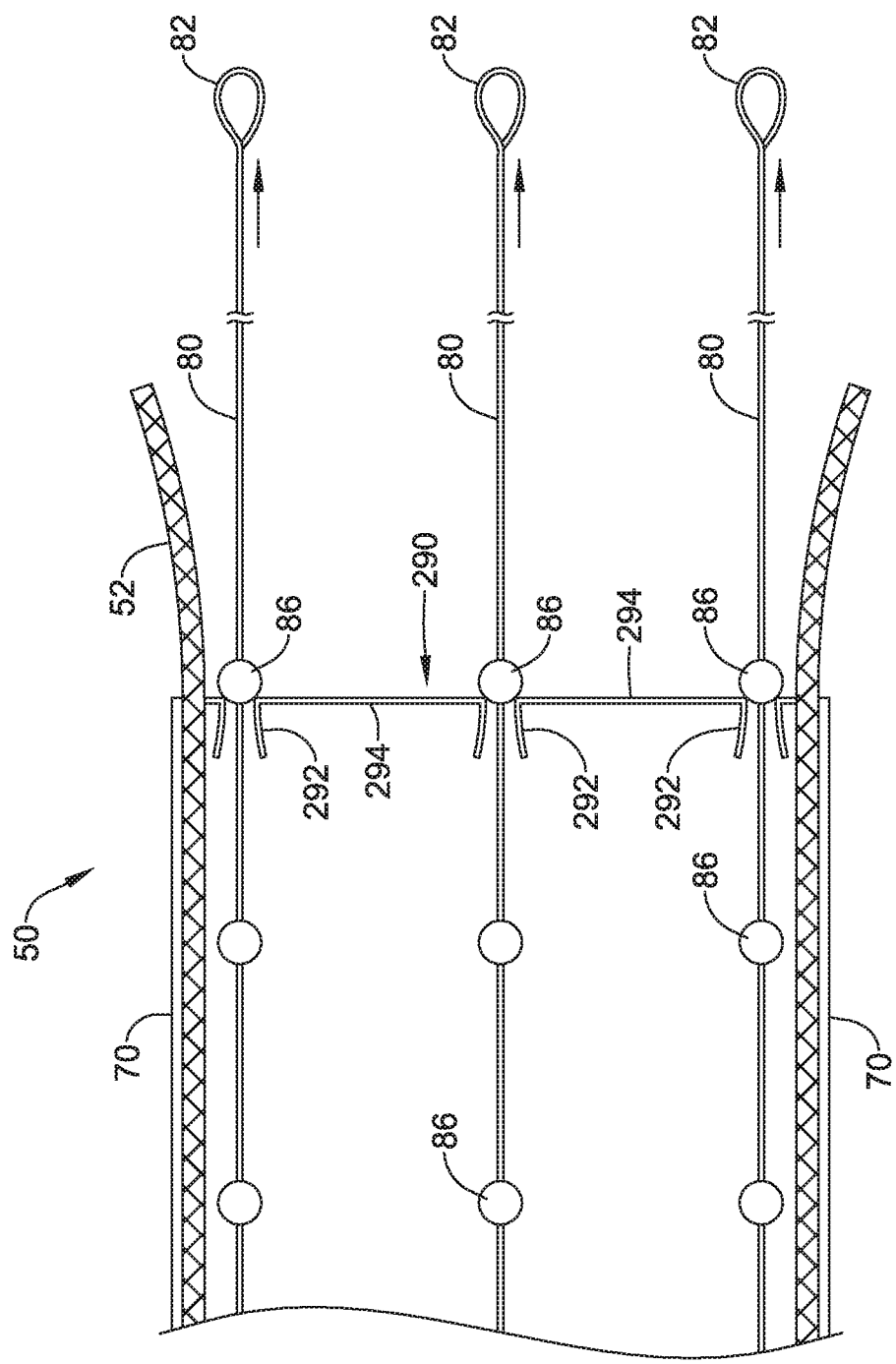

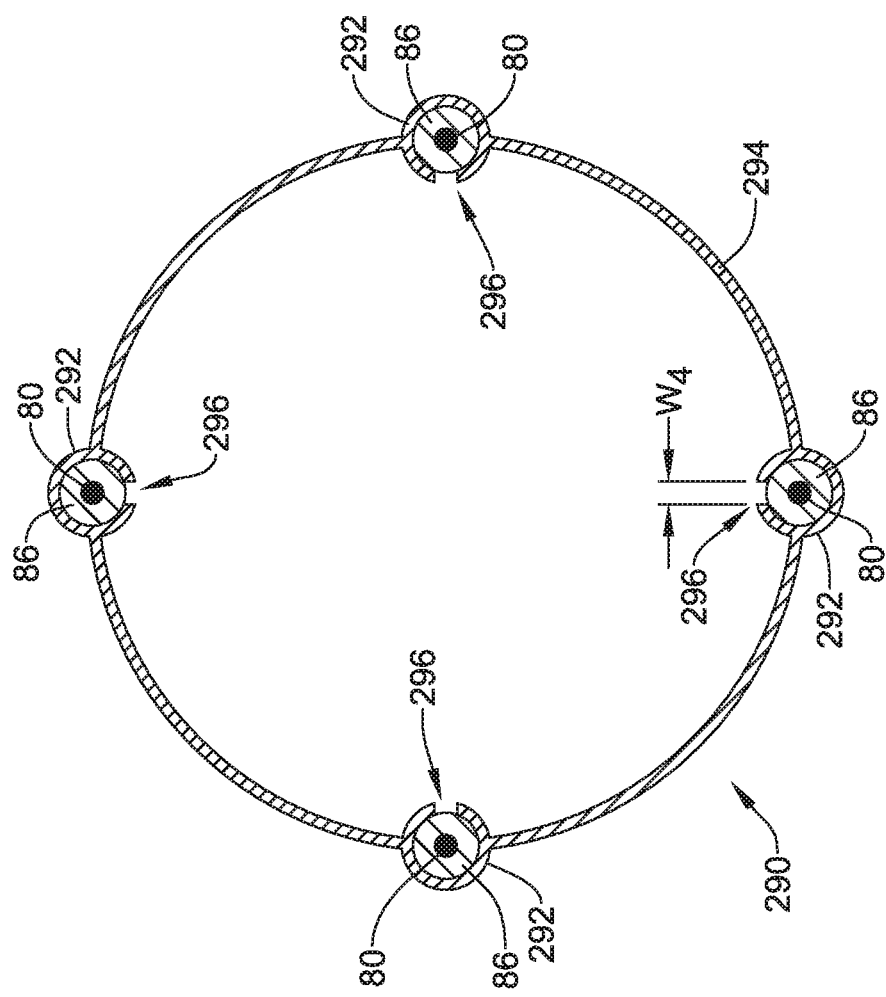

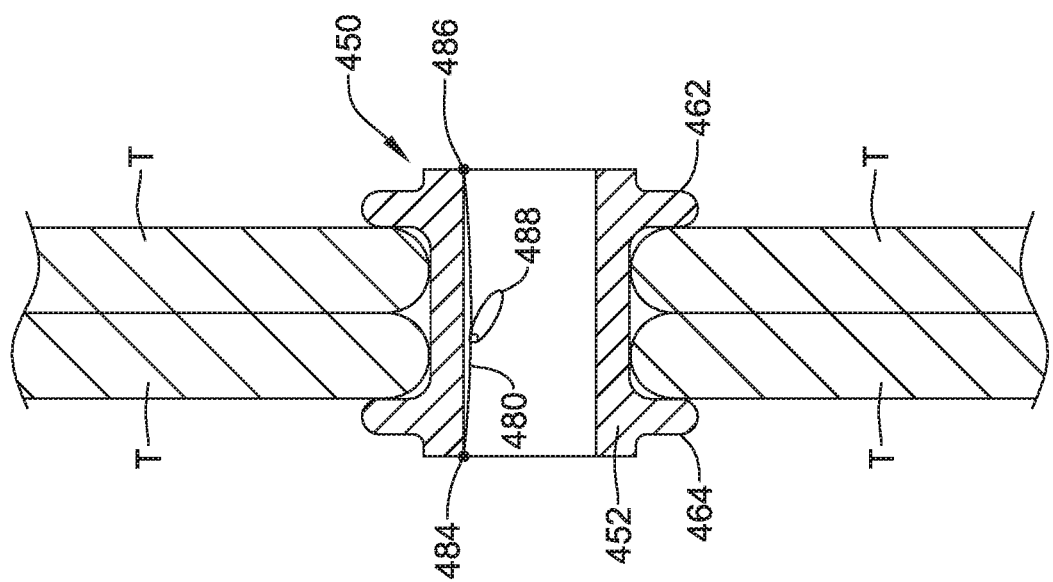

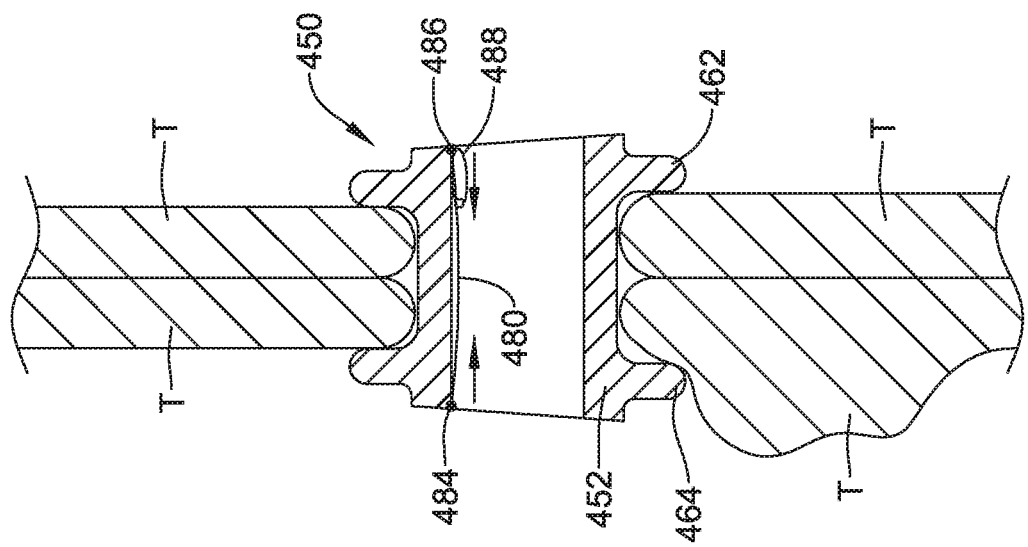

STENT WITH SELECTIVELY CURVED REGION

CROSS-REFERENCE TO RELATED APPLICATIONS

This application claims the benefit of priority under 35 U.S.C. § 119 of U.S. Provisional Application No. 62/680,731, filed Jun. 5, 2018, the entire disclosure of which is hereby incorporated by reference.

TECHNICAL FIELD

The present disclosure pertains to stent with a selectively curved region. More particularly, the present disclosure pertains a stent including a pull wire that can be manipulated to selective curve a region of the stent.

BACKGROUND

Stents may be spaced at various anatomical locations within a patient's body. For example, a stent may be placed in a patient's gastrointestinal tract during or following a bariatric surgical procedure. In some instances, the stent may be used to treat or mitigate leakage along a staple line created during the bariatric surgical procedure and/or can reduce irritation of healing tissue by nutritional contents. Accordingly, there is an ongoing need to provide alternative stents as well as alternative methods for manufacturing and using stents for bariatric surgical needs and/or conform to the post bariatric surgery anatomy of a patient.

BRIEF SUMMARY

This disclosure provides design, material, manufacturing method, and use alternatives for stents.

In a first example, a stent includes a radially expandable tubular framework, a covering, and a first drawstring. The radially expandable tubular framework has a proximal end, a distal end, and a lumen extending therethrough along a central longitudinal centerline. The covering surrounds the tubular framework. The first drawstring has a first end and a second end, with the first end of the first drawstring attached to the tubular framework at a first attachment location proximate the distal end of the tubular framework. The second end of the first drawstring is manipulatable proximate the proximal end of the tubular framework to deflect the tubular framework to move the central longitudinal centerline of the tubular framework into a curved configuration.

Alternatively or additionally to any of the examples above, in another example, the first drawstring extends along the tubular framework between an inner surface of the covering and an outer surface of the tubular framework.

Alternatively or additionally to any of the examples above, in another example, a distal end region of the covering is affixed to the tubular framework at a first affixment location and a proximal end region of the covering is affixed to the tubular framework at a second affixment location. The second affixment location is spaced proximally away from the first affixment location. The covering surrounds but is not directly affixed to the tubular framework between the first affixment location and the second affixment location.

Alternatively or additionally to any of the examples above, in another example, the first drawstring passes radially inward of the first affixment location as the first drawstring passes distally from the first affixment location to the attachment location.

Alternatively or additionally to any of the examples above, in another example, the first drawstring passes radially inward of the second affixment location as the first drawstring passes proximally from the second affixment location to the proximal end of the tubular framework.

Alternatively or additionally to any of the examples above, in another example, the stent further includes a second drawstring having a first end and a second end. The first end of the second drawstring is attached to the tubular framework at a second attachment location proximate the distal end of the tubular framework. The second attachment location is circumferentially spaced apart from the first attachment location around a circumference of the tubular framework.

Alternatively or additionally to any of the examples above, in another example, the stent further includes a third drawstring having a first end and a second end. The first end of the third drawstring is attached to the tubular framework at a third attachment location proximate the distal end of the tubular framework. The third attachment location is circumferentially spaced apart from the first and second attachment locations around the circumference of the tubular framework.

Alternatively or additionally to any of the examples above, in another example, the first, second and third attachment locations are spaced about 120° apart about the circumference of the tubular framework.

Alternatively or additionally to any of the examples above, in another example, the stent further includes a fourth drawstring having a first end and a second end. The first end of the fourth drawstring is attached to the tubular framework at a fourth attachment location proximate the distal end of the tubular framework. The fourth attachment location is circumferentially spaced apart from the first, second and third attachment locations around the circumference of the tubular framework.

Alternatively or additionally to any of the examples above, in another example, the first, second, third and fourth attachment locations are spaced about 90° apart about the circumference of the tubular framework.

Alternatively or additionally to any of the examples above, in another example, the stent further includes a locking mechanism proximate the proximal end of the tubular framework. The locking mechanism is configured to hold the first drawstring in tension with the tubular framework in the curved configuration.

Alternatively or additionally to any of the examples above, in another example, the locking mechanism includes a filament wrapped around the first drawstring to form a hitch knot.

Alternatively or additionally to any of the examples above, in another example, the first drawstring is movable through the hitch knot in a proximal direction, but the hitch knot prevents the first drawstring from moving through the hitch knot in a distal direction.

Alternatively or additionally to any of the examples above, in another example, the first drawstring includes either one or more nodes positioned along a length of the first drawstring, wherein the one or more nodes are configured to selectively engage the locking mechanism, or one or more loops positioned along a length of the first drawstring, wherein the one or more loops are configured to selectively engage the locking mechanism.

Another illustrative embodiment is a stent including a radially expandable tubular framework, a covering and a drawstring. The radially expandable tubular framework has a proximal end, a distal end, and a lumen extending therethrough along a central longitudinal centerline. The tubular framework is formed of one or more filaments. The covering surrounds a medial region of the tubular framework such that a proximal end region of the tubular framework extends proximal of the covering and is devoid of any covering. A distal end region of the tubular framework extend distal of the covering and is also devoid of any covering. The drawstring has a first end secured to the one or more filaments of the tubular framework at a first attachment location. A second end of the drawstring is manipulatable proximate the proximal end of the tubular framework to deflect the tubular framework to move the central longitudinal centerline of the tubular framework into a curved configuration.

Alternatively or additionally to any of the examples above, in another example, the drawstring extends along the tubular framework between an inner surface of the covering and an outer surface of the tubular framework.

Alternatively or additionally to any of the examples above, in another example, the stent includes a filament wrapped around the drawstring to form a hitch knot, wherein the drawstring is movable through the hitch knot in a proximal direction, but the hitch knot prevents the drawstring from moving through the hitch knot in a distal direction.

Alternatively or additionally to any of the examples above, in another example, the drawstring includes a plurality of nodes positioned along a length of the drawstring, wherein the plurality of nodes are configured to selectively engage a locking mechanism to retain the tubular framework in the curved configuration.

Alternatively or additionally to any of the examples above, in another example, the drawstring includes a plurality of loops positioned along a length of the drawstring, wherein the plurality of loops are configured to selectively engage a locking mechanism to retain the tubular framework in the curved configuration.

Another illustrative embodiment is a method of implanting a stent into a gastrointestinal tract of a patient subsequent a bariatric surgical procedure. The method includes pulling a drawstring of a stent to deflect a tubular framework of the stent into a curved configuration such that a central longitudinal centerline of the stent extends in an arcuate path. Thereafter, the drawstring is secured with the drawstring held in tension to maintain the curved configuration. The stent is positioned into a remaining stomach portion of the patient with the tubular framework in the curved configuration.

Another illustrative embodiment is a method of implanting a stent into a gastrointestinal tract of a patient subsequent a bariatric surgical procedure. The method includes pulling a drawstring of the stent to deflect the tubular framework of the stent to move the central longitudinal centerline of the tubular framework into a curved configuration, and positioning the stent into a remaining stomach portion of the patient with the tubular framework in the curved configuration.

The above summary of some embodiments is not intended to describe each disclosed embodiment or every implementation of the present disclosure. The Figures, and Detailed Description, which follow, more particularly exemplify some of these embodiments.

BRIEF DESCRIPTION OF THE DRAWINGS

The disclosure may be more completely understood in consideration of the following detailed description in connection with the accompanying drawings, in which:

FIG. 9A is a cross-sectional view taken along plane A-A of FIG. 8B;

FIG. 9B is a cross-sectional view taken along plane B-B of FIG. 8B;

FIG. 10A is a schematic illustration of the stent of FIG. 3 placed in a sleeve portion of a stomach following a gastric sleeve procedure;

FIG. 10B is a schematic illustration of the stent of FIG. 3 placed in a pouch portion of a stomach following a Roux-en-Y procedure;

FIG. 12 illustrates another exemplary locking mechanism for retaining the drawstring of the stent of FIG. 3 in a tensioned state;

FIG. 12A is a transverse cross-sectional view taken through the locking mechanism of FIG. 12;

FIGS. 15A and 15B illustrate aspects of an alternative stent configured to connect luminal passages of adjacent body lumens.

Figure 1:
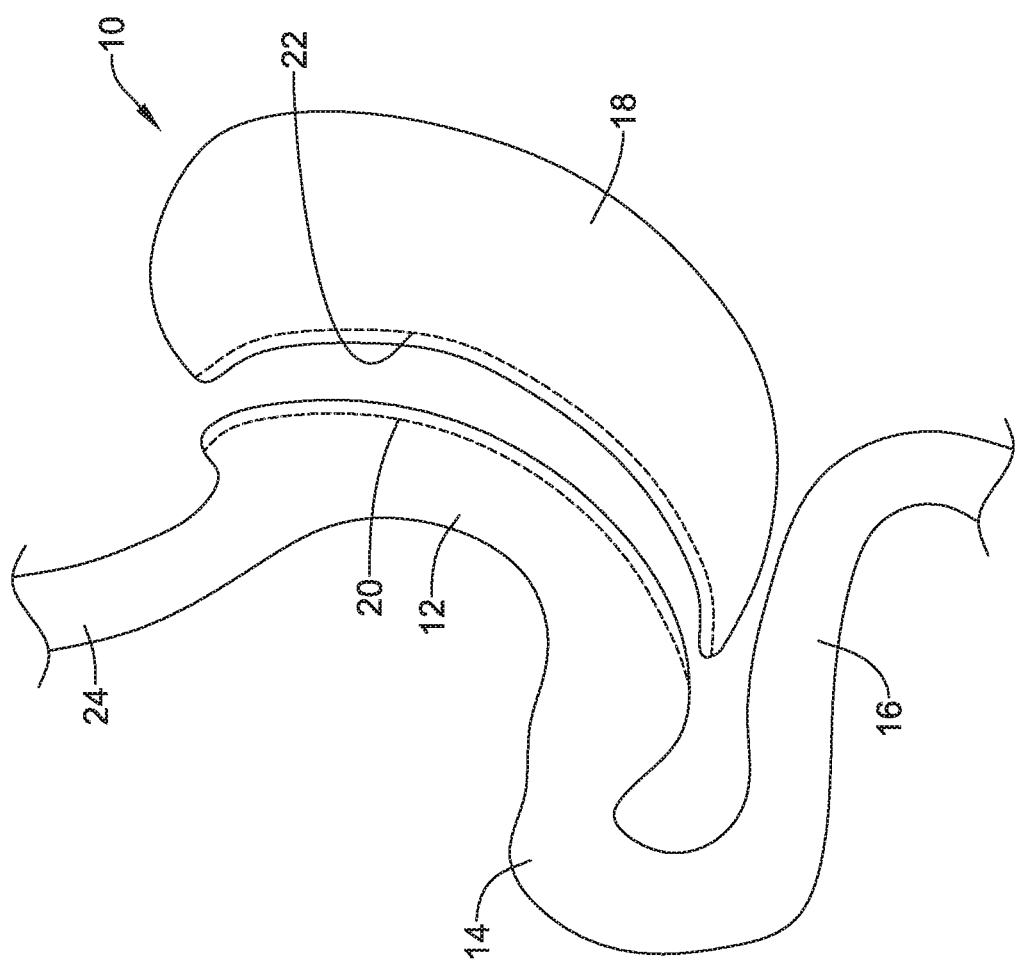
FIG. 1 is a schematic illustration of a gastric sleeve procedure.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar structures in different drawings are numbered the same. The drawings, which are not necessarily to scale, depict illustrative embodiments and are not intended to limit the scope of the disclosure.

There are a number of conditions, diseases and surgical interventions that may result in wounds such as a leak or an abscess within the gastrointestinal tract. In many cases, a surgical intervention may create a staple line or suture line within a portion of the gastrointestinal tract. An illustrative but non-limiting example of such a surgical intervention is bariatric surgery. In bariatric surgery, which may be performed as an open surgery or more commonly as a laparoscopic surgery, an obese patient's stomach is made substantially smaller. As a result, the patient may be able to lose weight, particularly if they follow corresponding dietary restrictions. There are several common bariatric techniques including sleeve gastrectomy and Roux-en-Y.

FIG. 1 illustrates the results of a sleeve gastrectomy, in which a large portion of a patient's stomach 10 is cut away. As a result, a relatively small attached portion 12 of the patient's stomach 10 remains fluidly coupled through the pylorus 14 with the small intestine 16. As can be seen in FIG. 1, a relatively large resected portion 18 of the patient's stomach 10 is resected, or cut away from the attached portion 12 of the patient's stomach 10 that remains as part of the patient's effective gastrointestinal tract and extends from the esophagus 24 to the small intestine 16 It will be appreciated that as a result of the resection, a large staple line 20 is formed along one side of the small portion 12 of the patient's stomach 10. In some instances, a corresponding long staple line 22 may be formed along one side of the resected portion 18 of the patient's stomach 10.

Figure 2:
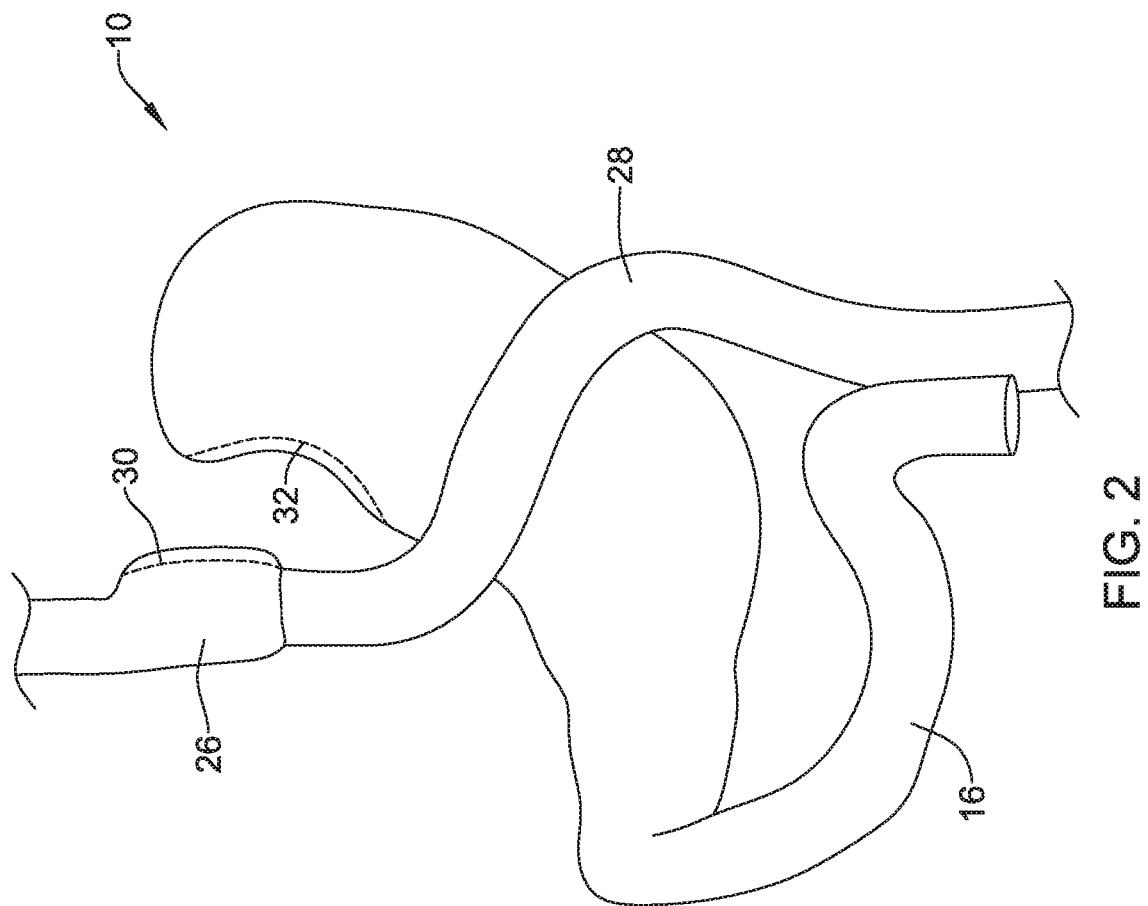
FIG. 2 is a schematic illustration of a Roux-en-Y procedure.

FIG. 2 illustrates the Roux-en-Y gastric bypass procedure in which an even larger portion of the patient's stomach 10 is resected and a portion of the small intestine 16 is also bypassed. In this procedure, a pouch 26 is formed from the very uppermost portion of the stomach 10 and is secured to the Roux limb 28, which is a portion of the small intestine 16 that is secured to the pouch 26. It will be appreciated that as a result of the resection, a staple line 30 is formed along one side of the pouch 26. A corresponding staple line 32 is formed along one side of the stomach 10.

It will be appreciated that leaks may occur along these staple lines, including the staple line 20 and the staple line 30. As a result, in some cases a pus-filled abscess may form adjacent the staple line 20 and/or the staple line 30. In some cases, it can be beneficial to place a stent, which in some cases may be a covered stent, proximate the wound in order to help seal off the leak, protect the wound from harsh stomach acids and keep nutritional contents such as food and beverages away from the wound. While leaks may occur along the staple line 22 and/or the staple line 32, it will be appreciated that this disclosure is directed to treating wounds that may be reached from inside the remaining gastrointestinal tract.

Figure 3:
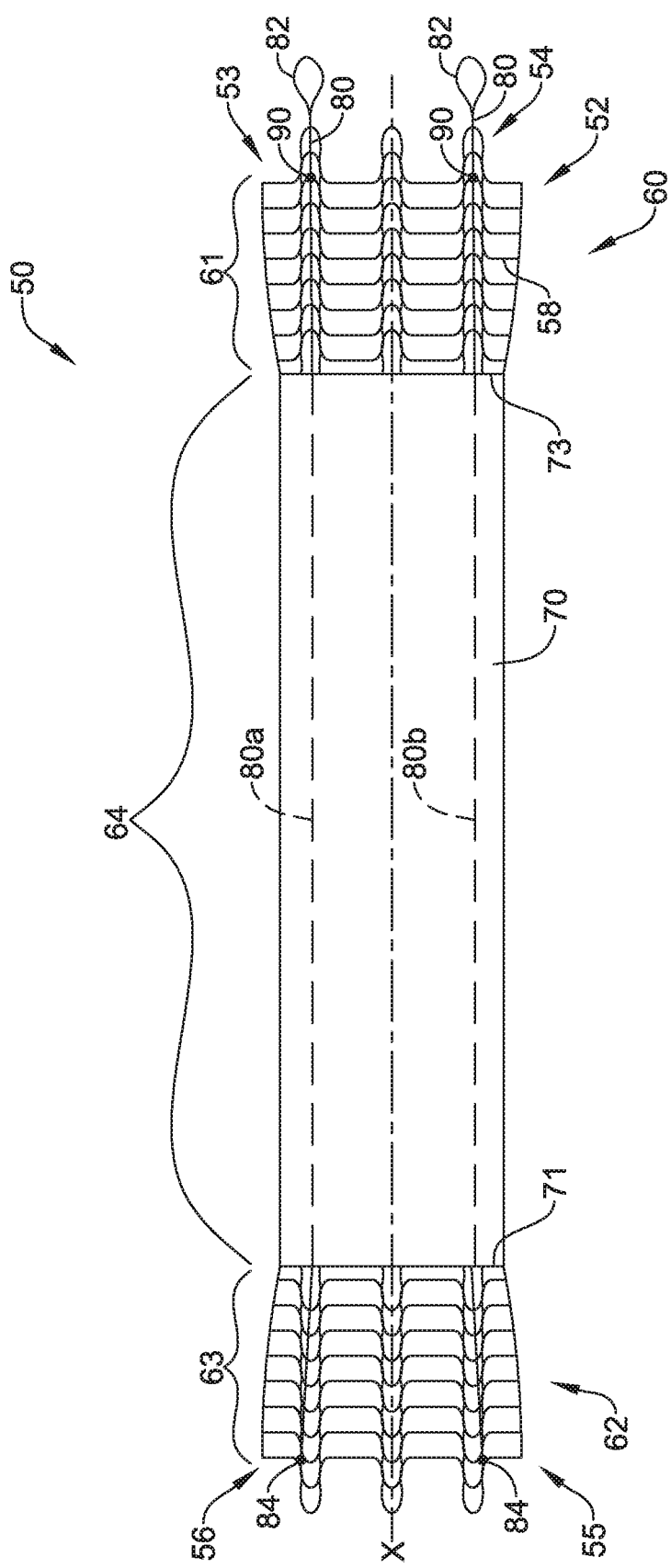
FIG. 3 is a side view of an exemplary stent having a drawstring to selectively manipulate the stent into a curved configuration.

FIG. 3 shows an example stent 50 having a first end 53 and a second end 55 opposite the first end 53. The stent 50 may include a tubular scaffold 52 having a first end 54, which may be considered a proximal end in some instances, a second end 56, which many be considered a distal end in some instances, and a lumen extending therethrough. The first end 54 may be located proximate the first end 53 of the stent 50 and the second end 56 may be located proximate the second end 55 of the stent 50. The tubular scaffold 52 may be configured to provide the support structure for the stent 50. The tubular scaffold 52 may be formed of one or more stent filaments 58, or a plurality of stent filaments 58. The filament(s) 58 may extend longitudinally along the stent 50.

In some instances, the stent 50 may be a self-expanding stent in which the one or more filaments 58 are interwoven to form the tubular scaffold 52, having openings defined between adjacent filaments 58. For example, stent filaments 58 may be wires braided, knitted or otherwise interwoven to form the tubular scaffold 52. Openings or interstices through the wall of the tubular scaffold 52 may be defined between adjacent stent filaments 58. Alternatively, the tubular scaffold 52 of the stent 50 may be a monolithic structure formed from a cylindrical tubular member, such as a single, cylindrical tubular laser-cut Nitinol tubular member, in which the remaining portions of the tubular member form the stent struts with openings defined therebetween.

Additionally, FIG. 3 shows the example stent 50 including one or more enlarged portions (e.g., flares) of the expandable scaffold 52 proximate the first end 54 and/or the second end 56. For instance, the stent 50 may include a first flared region 60 at the first, proximal end region 61 of the expandable scaffold 52 extending to the first end 54 of the expandable scaffold 52 and/or a second flared region 62 at the second, distal end region 63 of the expandable scaffold 52 extending to the second end 56 of the expandable scaffold 52. In some instances, the enlarged or flared regions 60/62 may be defined as an increase in the outer diameter, the inner diameter or both the inner and outer diameter of the expandable scaffold 52 relative to a medial region 64 of the expandable scaffold 52 positioned between the first and second flared regions 60/62. In some instances, the medial region 64 may be a cylindrical region of the expandable scaffold 52 extending from the first flared region 60 to the second flared region 62 having an outer diameter less than an outer diameter of the first and second flared regions 60/62. In other instances, the medial region 64 may be a cylindrical region of the expandable scaffold 52 extending from the first flared region 64 to the second end 56 of the expandable scaffold 52 having an outer diameter less than an outer diameter of the first flared region 60. The flared regions 60/62 may be beneficial to anchor the stent 50 within the esophagus and/or the opening to the stomach, for example.

The tubular scaffold 52, such as the filaments 58, disclosed herein may be constructed from a variety of materials. For example, the tubular scaffold 52, or components thereof, may be constructed from a metal (e.g., Nitinol). In other instances, the tubular scaffold 52, or components thereof, may be constructed from a polymeric material (e.g., PET). In yet other instances, the tubular scaffold 52, or components thereof, may be constructed from a combination of metallic and polymeric materials. Additionally, the tubular scaffold 52, or components thereof, may include a bioabsorbable and/or biodegradable material.

Additionally, the stent 52 may include a covering 70 disposed on the tubular scaffold 52, such as positioned on and/or adjacent to the outer surface of the tubular scaffold 52 to thereby surround the tubular scaffold 52. The covering 70 may be positioned on a portion of the filaments 58 forming the tubular scaffold 52 and extend across openings or cells between adjacent filaments 58. In some instances, the covering 70 may be an elastomeric or non-elastomeric material. For example, the covering 70 may be a polymeric material, such as silicone, polyurethane, or the like. The covering 70 may isolate the lumen of the tubular scaffold 52 from the body lumen of the patient, thereby forming a barrier, such as a sealed interface, between the lumen of the tubular scaffold 52 and the portion of the body lumen positioned radially outward of the covering 70.

As described above, the stent 50 may have a first end 53 and a second end 55. When positioned in a body lumen (e.g., esophagus, stomach, stomach pouch, intestine, etc.) the first end 53 may be defined as the proximal end of the stent 50 and oriented as the end of the stent 50 closest to a patient's mouth and the second end 55 may be defined as the distal end of the stent 50 and oriented as the end of stent 50 closest to a patient's stomach.

As shown in FIG. 3, the covering 70 may be fixedly attached to the expandable scaffold 52 at one or more affixment locations. For instance, the covering 70 may be affixed to the expandable scaffold 52 at a first affixment location 71 and/or at a second affixment location 73. The first and second affixment locations 71/73 may be spaced apart from one another with the second affixment location 73 closer to the first, proximal end 53 of the stent 50 than the first affixment location 71, and the covering 70 extending between the first and second affixment locations 71/73 and circumferentially surrounding the expandable scaffold 52 between the first and second affixment locations 71/73. In some instances, the covering 70 may not be directly affixed to the tubular scaffold 52 between the first and second affixment locations 71/73. In some instances, the covering 70 may be affixed to the tubular scaffold 52 continuously around the entire circumference of the tubular scaffold 52 at the first and second affixment locations 71/73, or the covering 70 may be affixed at discrete circumferentially spaced locations around the circumference of the tubular scaffold 52 at the first and second affixment locations 71/73. In some embodiments, the covering 70 may be affixed to the expandable scaffold 52 with an adhesive at the first and/or second affixment locations 71/73. The first and second affixment locations 71/73 may be located intermediate the first and second ends 54/56 of the tubular scaffold 52, such that the tubular scaffold 52 extends proximal of the affixment location 73 toward the first, proximal end 53 of the stent 50, and the tubular scaffold 52 extends distal of the affixment location 71 toward the second, distal end 55 of the stent 50. For example, the first affixment location 71 may be located between the distal end region 63 and the medial region 64 of the tubular scaffold 52, and the second affixment location 73 may be located between the medial region 64 and the proximal end region 61 of the tubular scaffold 52. The covering 70 may extend proximal of the first affixment location 71 toward the first end 53 of the stent 10 and may extend distal of the second affixment location 73 toward the second end 55 of the stent 10, and circumferentially surround the medial region 64 of the expandable scaffold 52. The proximal end of the covering 70 may be affixed to the expandable scaffold 52 at the second affixment location 73 and the distal end of the covering 70 may be affixed to the expandable scaffold 52 at the first affixment location 71. In some instances the second affixment location 73, and thus the proximal end of the covering 70, may be located proximate the junction between the medial region 64 and the proximal end region 61, and thus the flared end region 60, of the expandable scaffold 52, leaving the proximal end region 61, and thus the proximal flared end region 60 uncovered. Thus, the proximal end region 61 may be devoid of any covering and thereby permit tissue ingrowth through interstices or openings of the expandable scaffold 52 between adjacent filaments 58. Additionally or alternatively, the first affixment location 71, and thus the distal end of the covering 70, may be located proximate the junction between the medial region 64 and the distal end region 63, and thus the flared end region 62, of the expandable scaffold 52, leaving the distal end region 63, and thus the distal flared end region 62 uncovered. Thus, the distal end region 63 may be devoid of any covering and thereby permit tissue ingrowth through interstices or openings of the expandable scaffold 52 between adjacent filaments 58. In other words, in some instances the covering 70 may extend less than the entire length of the stent 50, if desired, leaving a portion of cells or interstices defined between filaments 58 of tubular scaffold 52 unfilled or open to promote hyperplastic tissue ingrowth. However, in other instances the covering 70 may extend to the proximal end of the stent 50 and surround the proximal flared region 60 and/or the covering 70 may extend to the distal end of the stent 50 and surround the distal flared region 62, if desired.

The stent 50 may extend along a central longitudinal centerline X. The central longitudinal centerline X may be centrally located within the lumen of the stent 50 at any transverse cross-sectional location. In other words, at any cross-section taken perpendicular to the longitudinal centerline X, the longitudinal centerline X will be centered within the tubular framework 52, and thus centered within the stent 50. As will be discussed further herein, the central longitudinal centerline X may extend linearly when the stent 50 is in a straight, natural configuration in which the stent 50 is not subjected to any deflection forces (e.g., when the drawstrings 80 discussed herein are not placed in tension). When subjected to a deflection force (e.g., by tensioning one or more of the drawstrings 80 discussed herein), the central longitudinal centerline X may be moved into a curved configuration, thus placing the tubular framework 52, and thus the stent 50, into a curved configuration.

The stent 50 may include one or more, or a plurality of drawstrings 80 extending along the stent 50 to selectively move the stent 50 into a curved configuration. In some instances, the stent 50 may include one drawstring 80. In other instances, the stent 50 may include a first drawstring 80*a* and a second drawstring 80*b* with the respective attachment locations being circumferentially spaced apart from one another around a circumference of the tubular framework 52. For example, the attachment location 84 of the first drawstring 80*a* may be spaced 180 degrees around the circumference from the attachment location 84 of the second drawstring 80*b*. In other instances, the attachment location 84 of the first drawstring 80*a* may be spaced 90 degrees around the circumference from the attachment location 84 of the second drawstring 80*b*, allowing the stent 50 to be curved in two planes perpendicular to one another. In other instances (see FIG. 7), the stent 50 may include a first drawstring 80*a*, a second drawstring 80*b*, and a third drawstring 80*c* with the respective attachment locations being circumferentially spaced apart from one another around a circumference of the tubular framework 52. For example, the attachment location 84 of each of the first, second and third drawstrings 80*a*/80*b*/80*c* may be spaced 120 degrees around the circumference from one another, or the attachment location 84 of the second drawstring 80*b* may be spaced apart 90 degrees from the attachment locations 84 of each of the first and third drawstrings 80*a*/80*c*. In yet other instances (see FIG. 7), the stent 50 may include a first drawstring 80*a*, a second drawstring 80*b*, a third drawstring 80*c*, and a fourth drawstring 80*d*, with the respective attachment locations being circumferentially spaced apart from one another around a circumference of the tubular framework 52. For example, the attachment location 84 of each of the first, second, third and fourth drawstring 80 may be spaced 90 degrees around the circumference from one another. These arrangements are only exemplary and other arrangements of drawstrings 80 are contemplated to provide the desired ability to manipulate the curvature of the stent 50.

A distal end of the drawstring(s) 80 may be attached to the tubular framework 52 proximate the distal end 55 of the stent 50 and extend along the stent 50 to or beyond the proximal end 53 of the stent 50. For instance, a distal end of the drawstring(s) 80 may be attached to the tubular framework 52 at an attachment location 84 and a proximal end of the drawstring(s) 80 may include a pull 82, such as a loop, for grasping by medical personnel. In some instances, the distal end of the drawstring(s) 80 may be tied to the tubular framework 52, affixed with the tubular framework 52 with an adhesive, clamped to the tubular framework 52, or otherwise secured to the tubular framework 52. The drawstring(s) 80 may be manipulated by surgical personnel (e.g., pulled proximally relative to the tubular scaffold 52) to selectively curve the central longitudinal centerline X of the stent 50, thus placing the stent 50 in a curved configuration during a surgical procedure. For example, the drawstring(s) 80 may be pulled proximally to bend the stent 50 into a desired curved configuration.

Figure 4:
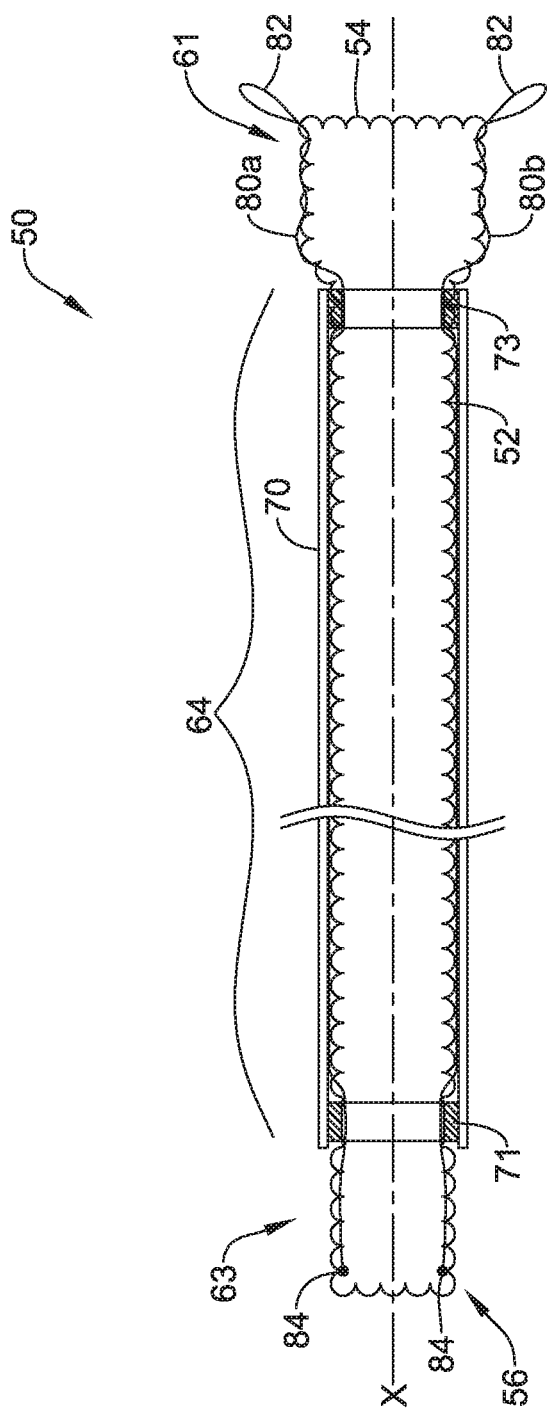
FIG. 4 is a longitudinal cross-sectional view of the stent of FIG. 3.

FIG. 4 is a cross-sectional view of the stent 50 of FIG. 3 showing one exemplary pathway for routing the drawstrings 80 along the stent 50. As shown in FIG. 4, in some instances, the drawstrings 80 may be woven in and out of the uncovered proximal end region 61 of the tubular scaffold 52 such that the drawstrings 80 pass radially outward of the tubular scaffold 52 and radially inward of the tubular scaffold 52 along the uncovered proximal region 61. In other instances, the drawstrings 80 may pass along an exterior of and thus radially outward of the uncovered proximal region 61, or the drawstrings 80 may pass along an interior of and thus radially inward of the uncovered proximal end region 61. The drawstrings 80 may pass radially inward of the second affixment location 73, and thus radially inward of the tubular scaffold 52, as the drawstrings 80 pass from the uncovered proximal region 61 to the covered medial region 64 of the tubular scaffold 52. Furthermore, the drawstrings 80 may pass radially outward through the tubular scaffold 52 distal of the second affixment location 73 such that the drawstrings 80 may extend radially inward of the covering 70 between the inner surface of the covering 70 and the outer surface of the expandable scaffold 52 throughout the medial region 64 of the expandable scaffold 52 between the first and second affixment locations 71/73. The drawstrings 80 may pass radially inward of the first affixment location 71, and thus radially inward of the tubular scaffold 52, as the drawstrings 80 pass the first affixment location 71 to the uncovered distal region 63. The drawstrings 80 may be woven in and out of the uncovered distal end region 63 of the tubular scaffold 52 such that the drawstrings 80 pass radially outward of the tubular scaffold 52 and radially inward of the tubular scaffold 52 along the uncovered distal region 63 as the drawstrings 80 are routed to the attachment location 84. In other instances, the drawstrings 80 may pass along an exterior of and thus radially outward of the uncovered distal region 63, or the drawstrings 80 may pass along an interior of and thus radially inward of the uncovered distal end region 63.

Figure 5A:
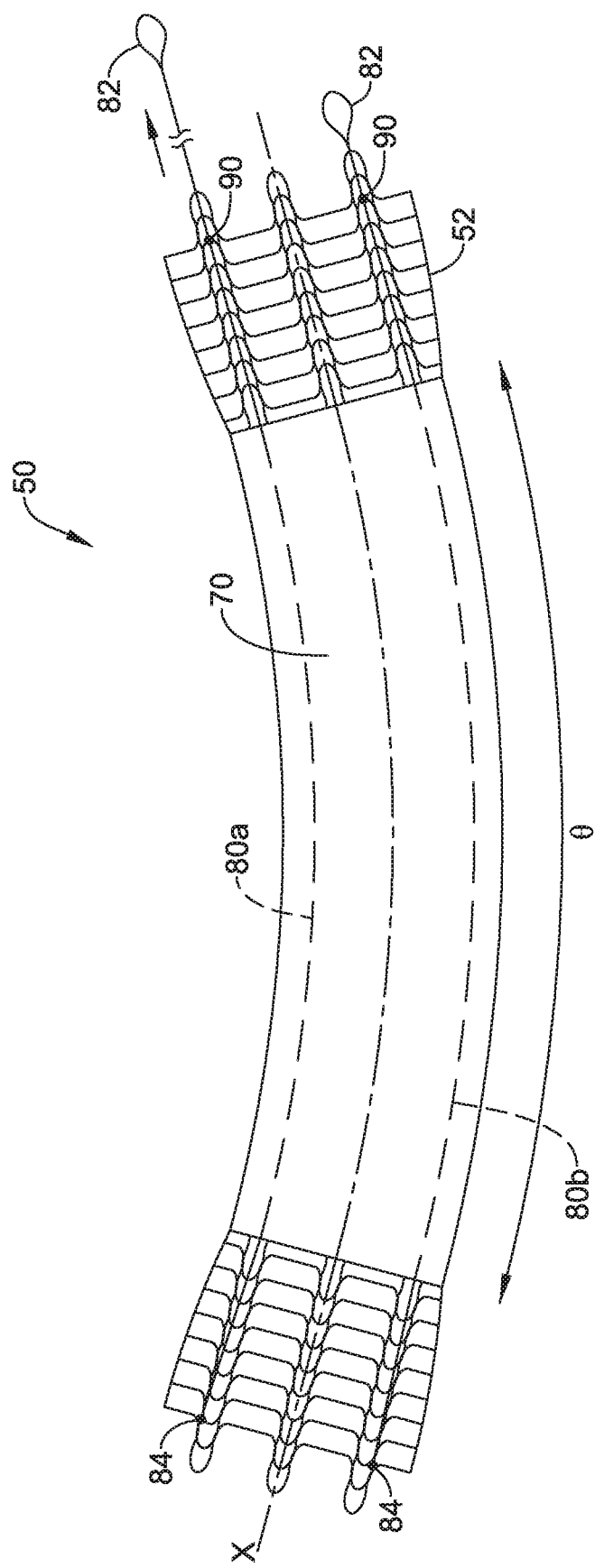
FIG. 5A is a side view of the exemplary stent of FIG. 3 in a first curved configuration.
Figure 5B:
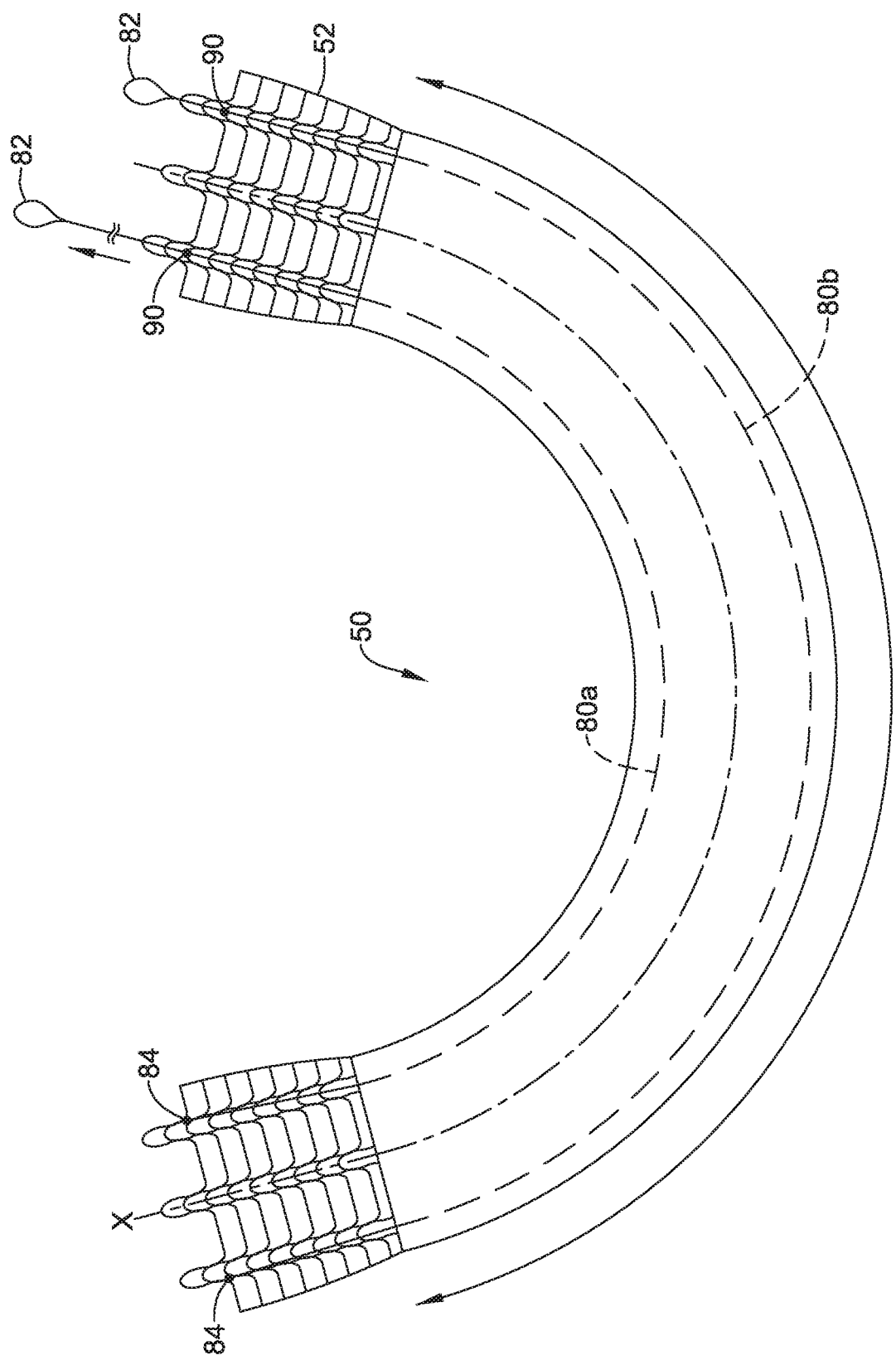
FIG. 5B is a side view of the exemplary stent of FIG. 3 in a second curved configuration.
Figure 5C:
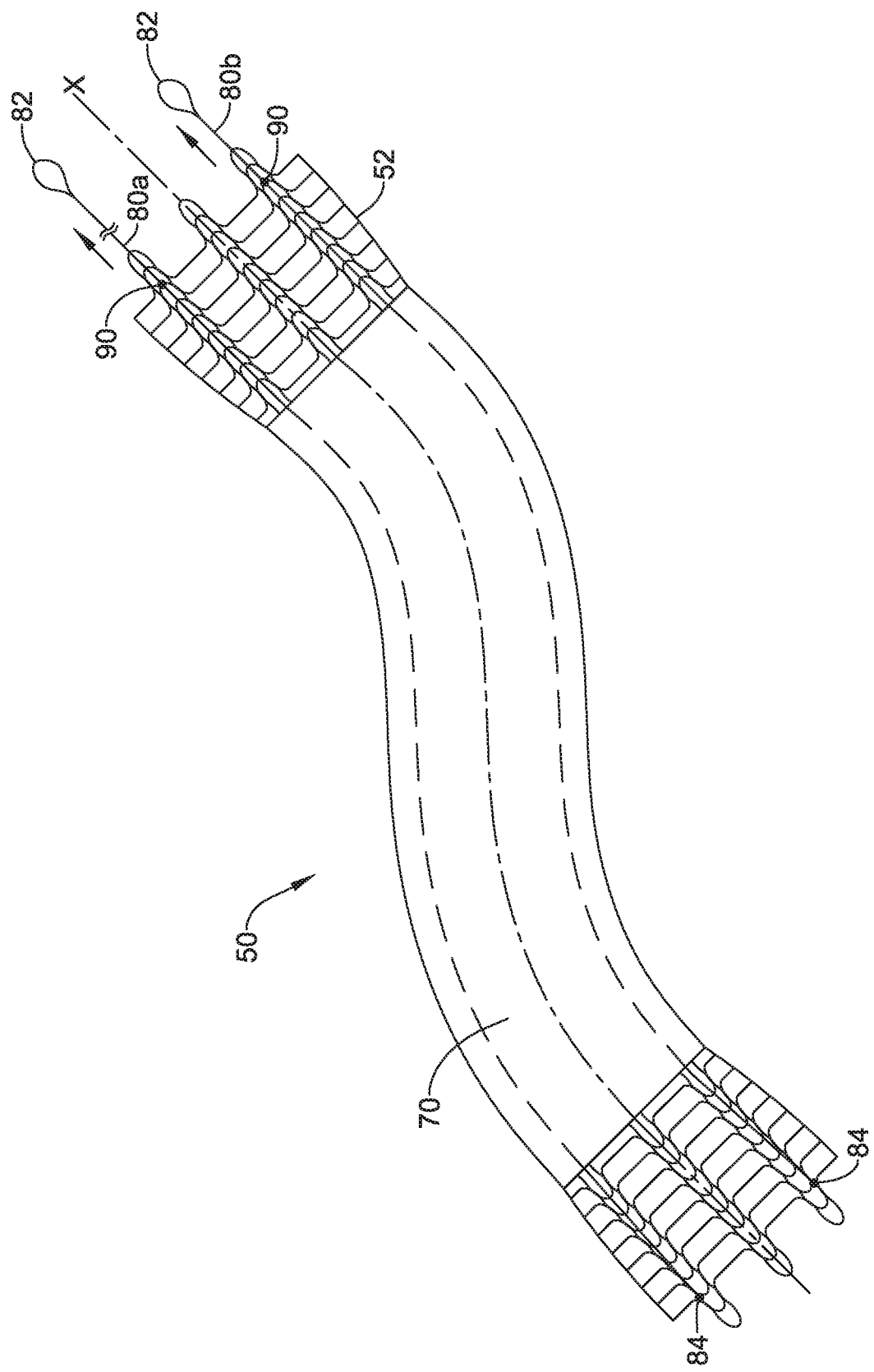
FIG. 5C is a side view of the exemplary stent of FIG. 3 in a third curved configuration.

As shown in FIGS. 5A-5C, one or more of the drawstrings 80 may be pulled proximally relative to the tubular scaffold 52 to bend or deflect the tubular scaffold 52, and thus the stent 50 into a desired curved configuration in which the central longitudinal centerline X is curved or nonlinear. For example, as shown in FIG. 5A, the first drawstring 80*a* may be pulled proximally relative to the tubular scaffold 52 to move the central longitudinal centerline X, and thus the stent 50, into a first curved configuration having angle of curvature θ. As shown in FIG. 5A, the angle of curvature θ may be an acute angle, giving the stent 50 a gentle curvature. In other instances, the first drawstring 80*a* may be pulled further proximally relative to the tubular scaffold 52 to move the central longitudinal centerline X, and thus the stent 50, into a second curved configuration having a greater angle of curvature θ, as shown in FIG. 5B. The angle of curvature θ may be a perpendicular angle, or an obtuse angle, giving the stent 50 a more aggressive curvature. In other instances, multiple drawstrings 80 may be pulled proximally relative to the tubular scaffold 52 to move the stent 50 into a compound curved configuration. A compound curved configuration is a configuration in which the stent 50 has multiple curved regions curving about a plurality of different apices of curvature. For instance, as shown in FIG. 5C, the stent 50 may have a first curved region having a first angle of curvature about a first apex of curvature and a second curved region having an second angle of curvature about a second apex of curvature different from the first apex of curvature. Such a compound curved configuration may be formed by selectively pulling multiple drawstrings 80. For instance, the first drawstring 80a and the second drawstring 80b may both be pulled proximally to move the stent 50 into a compound curved configuration.

Figure 6A:
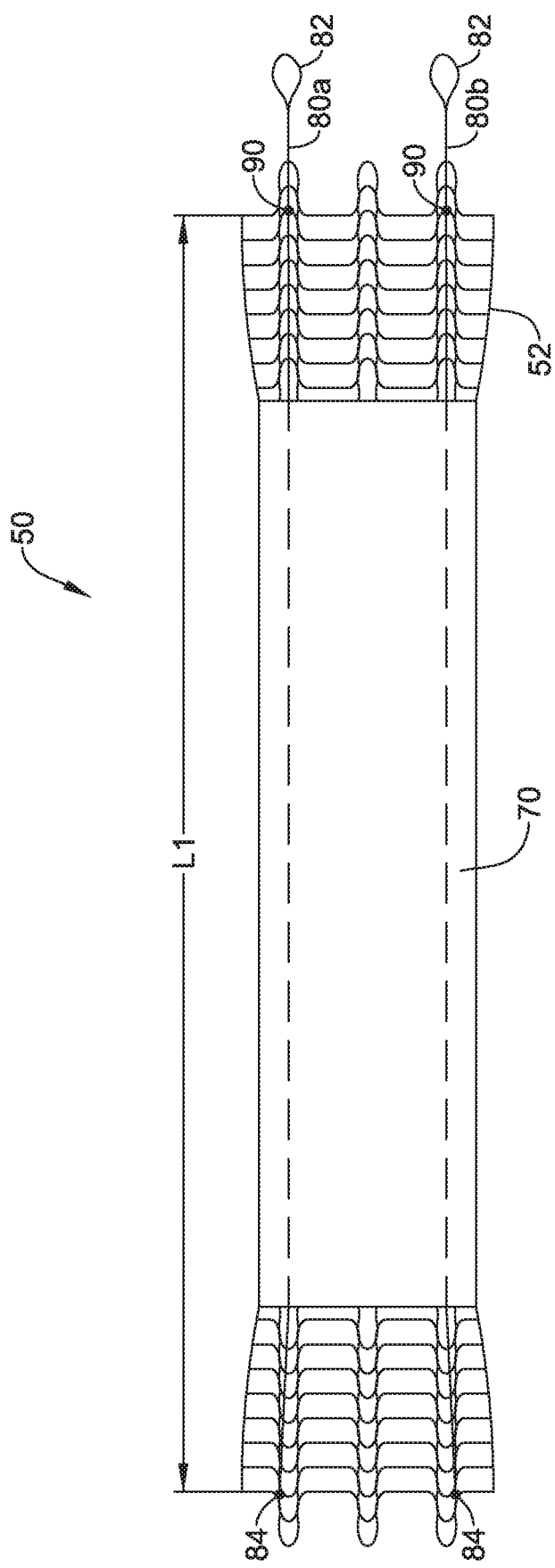
FIG. 6A is a side view of the exemplary stent of FIG. 3 with the stent at a first length.
Figure 6B:
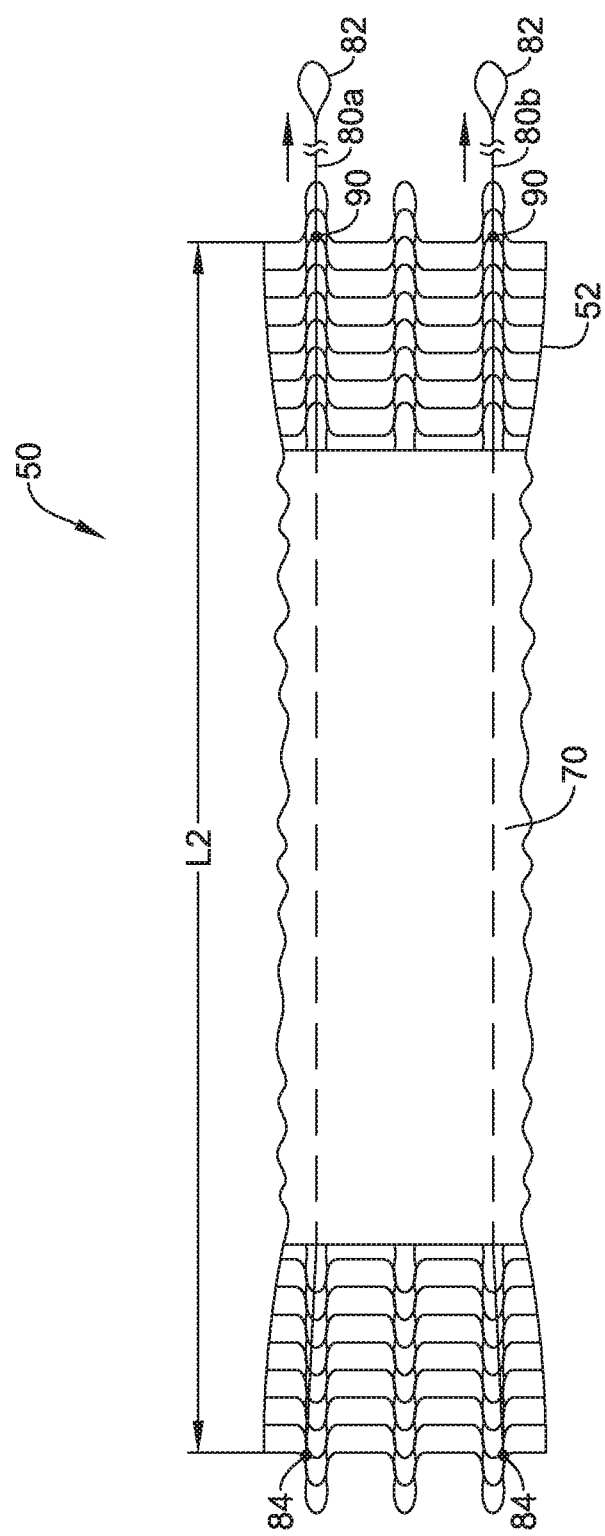
FIG. 6B is a side view of the exemplary stent of FIG. 3 with the stent at a second length.

An alternative arrangement of utilizing the drawstrings 80 is shown in FIGS. 6A and 6B. As shown in FIG. 6A, when the drawstrings 80a, 80b are untensioned the overall length of the stent 50 may have a nominal length L1. However, if it is desired to shorten the overall length of the stent 50, the drawstrings 80a, 80b may be pulled proximally, and thus tensioned, to reduce the overall length of the stent a longitudinally contracted length L2. Thus, the stent 50 may be manipulated during a surgical procedure to modify the overall length of the stent 50 to a desired length to accommodate placement at an anatomical location. It is also noted that shortening the overall length of the stent 50 may be used to stiffen the stent 50 or otherwise make the stent 50 more rigid to thereby reduce the lateral flexibility of the stent 50.

Figure 7:
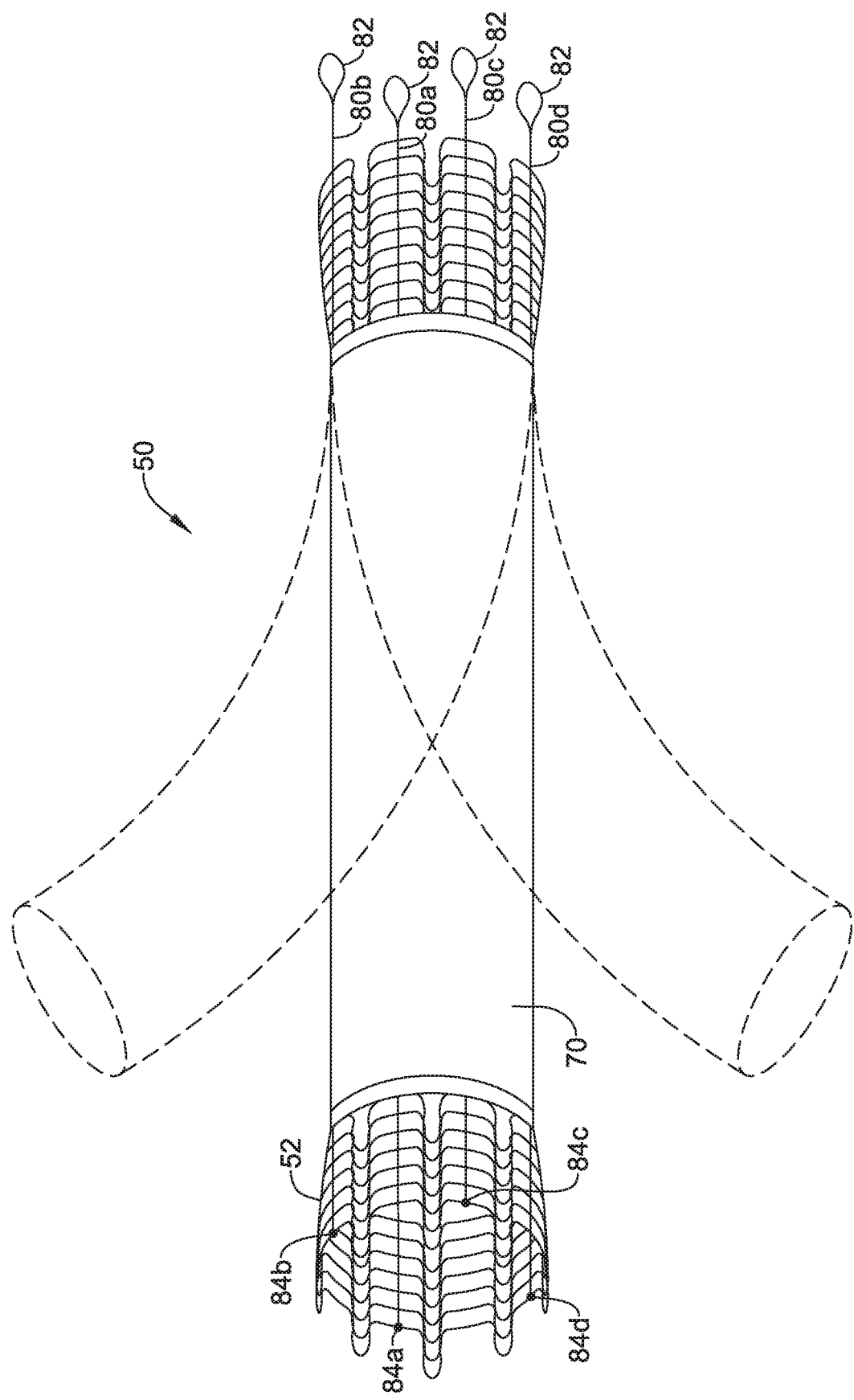
FIG. 7 is a perspective view of the stent of FIG. 3 with multiple drawstrings to selectively control the curvature of the stent.

FIG. 7 illustrates the stent 50 having a plurality of drawstrings 80 symmetrically arranged around the circumference of the stent 50. As shown in FIG. 7, the stent 50 may include a first drawstring 80a, a second drawstring 80b, a third drawstring 80c, and a fourth drawstring 80d extending longitudinally along the stent 50. The first drawstring 80a may have a distal end attached to the tubular framework 52 at a first attachment location 84a, the second drawstring 80b may have a distal end attached to the tubular framework 52 at a second attachment location 84b, the third drawstring 80c may have a distal end attached to the tubular framework 52 at a third attachment location 84c, and the fourth drawstring 80d may have a distal end attached to the tubular framework 52 at a fourth attachment location 84d. The first, second, third and fourth attachment locations 84a/84b/84c/84d may be circumferentially spaced apart from one another around a circumference of the tubular framework 52 proximate the distal end of the stent 50. For example, the attachment location 84 of each of the first, second, third and fourth drawstring 80 may be spaced apart 90 degrees around the circumference from one another. Manipulation (e.g., pulling) of one or more of the drawstrings 80 will cause the stent 50 to deflect or curve into a desired curved orientation. Two possible curved configurations are illustrated in dashed lines in FIG. 7. However, it is possible to place the stent 50 in any desired curved configuration by selectively manipulating one or more of the drawstrings 80.

Figure 8A:
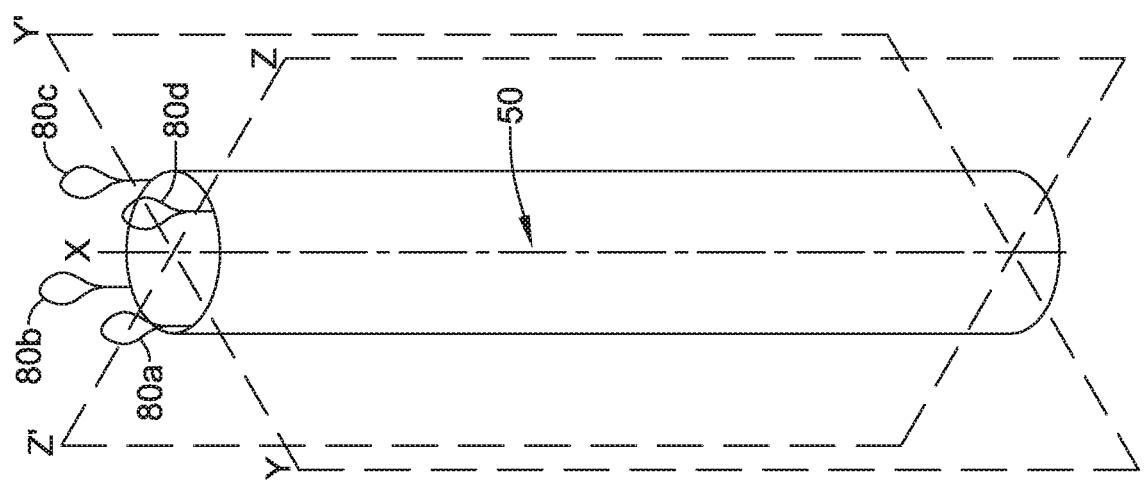
FIG. 8A is a schematic view of the stent of FIG. 3 in a straight configuration.

FIG. 8A illustrates the stent 50 having a plurality of drawstrings 80 symmetrically arranged around the circumference of the stent 50, similar to that shown in FIG. 7. As shown in FIG. 8A, the stent 50 may include a first drawstring 80a, a second drawstring 80b, a third drawstring 80c, and a fourth drawstring 80d extending longitudinally along the stent 50. The distal ends of the drawstrings 80a, 80b, 80c, and 80d may be spaced apart and attached to the tubular framework of the stent 50, similar to that described above. Manipulation (e.g., pulling) of one or more of the drawstrings 80 will cause the stent 50 to deflect or curve into a desired curved orientation.

The stent 50 is shown in a straight configuration in FIG. 8A in which the central longitudinal centerline X of the stent 50, centrally located within the lumen of the stent 50 at every transverse cross-sectional location, extends in a straight line. Thus, the central longitudinal centerline X may lie in a first plane Y-Y' extending parallel to the central longitudinal centerline X and lie a second plane Z-Z' extending parallel to the central longitudinal centerline X, wherein the second plane Z-Z' is perpendicular to the first plane Y-Y'. Thus, the first plane Y-Y' intersects the second plane Z-Z' along the central longitudinal centerline X, such that a line of intersection of the first plane Y-Y' and the second plane Z-Z' is located along the central longitudinal centerline X of the stent 50.

Figure 8B:
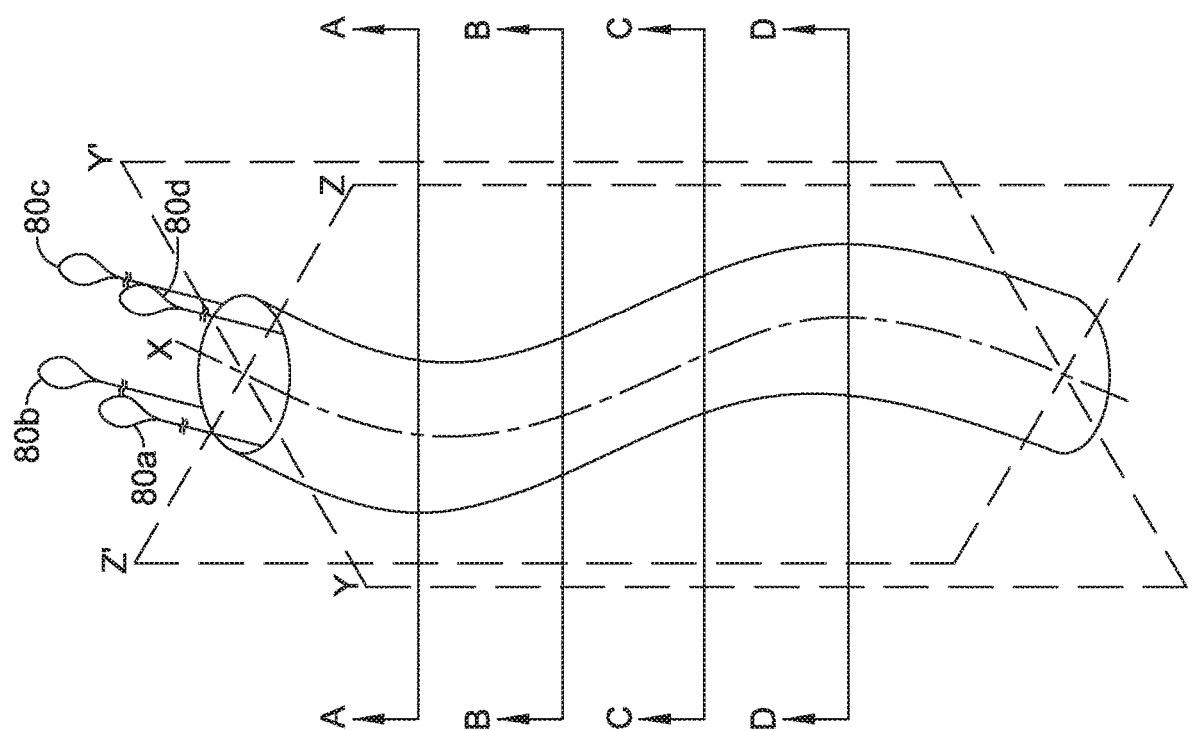
FIG. 8B is a schematic view of the stent of FIG. 3 in a compound curved configuration.

Manipulation (e.g., pulling) of one or more of the drawstrings 80a, 80b, 80c, 80d will cause the stent 50 to deflect or curve into a compound curved configuration. In a compound curved configuration, the central longitudinal centerline X of the stent 50 may be centered on the line of intersection of the first plane Y-Y' and the second plane Z-Z' at the first and second ends of the stent 50, while the central longitudinal centerline X moves away from (i.e., is offset from) the line of intersection of the first plane Y-Y' and the second plane Z-Z' in two or more longitudinally spaced apart locations along the length of the stent 50 between the first and second ends of the stent 50 to form multiple curved segments of the stent 50 having different directions of curvature, such as shown in FIG. 8B. As shown in FIG. 8B, in a compound curved configuration, the stent 50 may have a plurality of curved segments, each having a different apex of curvature.

Figure 9C:
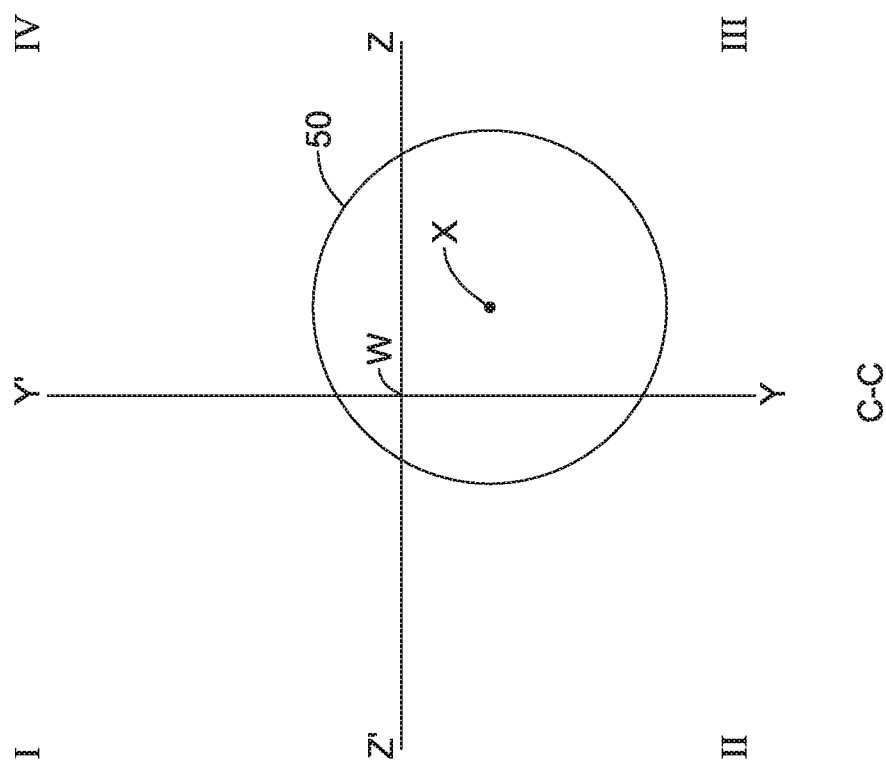
FIG. 9C is a cross-sectional view taken along plane C-C of FIG. 8B.
Figure 9D:
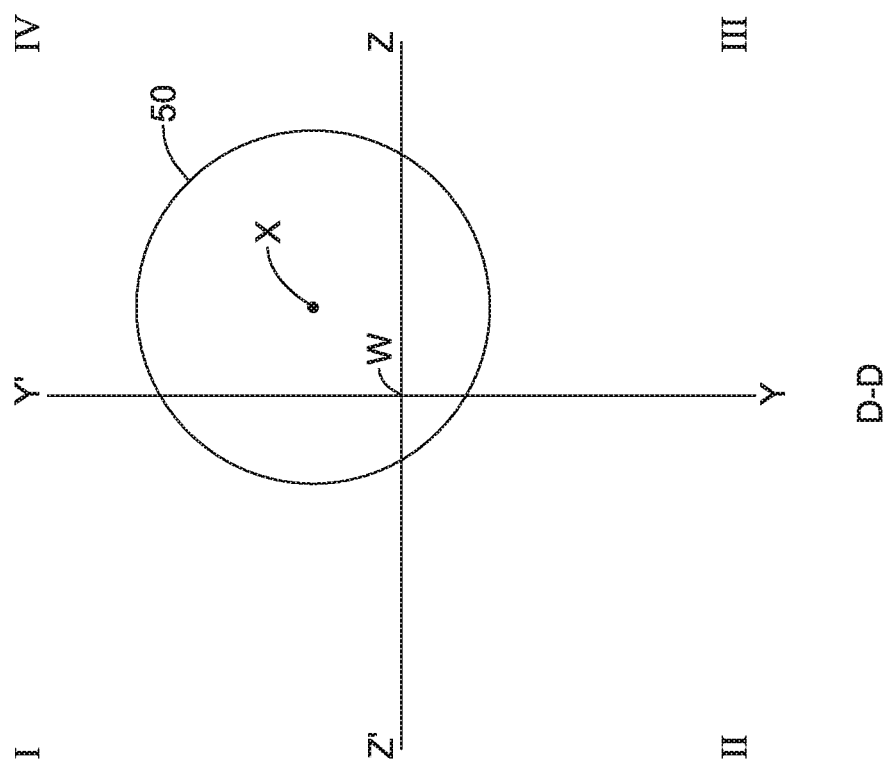
FIG. 9D is a cross-sectional view taken along plane D-D of FIG. 8B.

The cross-sectional views shown in FIGS. 9A-9D further illustrate the deflection of the central longitudinal centerline X of the stent 50 away from the line of intersection W of the first plane Y-Y' and the second plane Z-Z'. FIG. 9A is a cross-sectional view taken along plane A-A of FIG. 8B perpendicular to plane Y-Y' and plane Z-Z'. FIG. 9B is a cross-sectional view taken along plane B-B of FIG. 8B perpendicular to plane Y-Y' and plane Z-Z'. FIG. 9C is a cross-sectional view taken along plane C-C of FIG. 8B perpendicular to plane Y-Y' and plane Z-Z'. FIG. 9D is a cross-sectional view taken along plane D-D of FIG. 8B perpendicular to plane Y-Y' and plane Z-Z'. Plane B-B may be closer to the second end of the stent than plane A-A, plane C-C may be closer to the second end of the stent than plane B-B, and plane D-D may be closer to the second end of the stent than plane C-C. As shown in FIG. 9A, the central longitudinal centerline X of the stent 50 may be offset from the line of intersection W of the first plane Y-Y' and the second plane Z-Z' and located in a first quadrant (quadrant I) at a first cross-sectional location along the length of the stent 50 between the first and second ends. As shown in FIG. 9B, the central longitudinal centerline X of the stent 50 may be offset from the line of intersection W of the first plane Y-Y' and the second plane Z-Z' and located in a second quadrant (quadrant II) at a second cross-sectional location along the length of the stent 50 between the first and second ends. As shown in FIG. 9C, the central longitudinal centerline X of the stent 50 may be offset from the line of intersection W of the first plane Y-Y' and the second plane Z-Z' and located in a third quadrant (quadrant III) at a third cross-sectional location along the length of the stent 50 between the first and second ends. As shown in FIG. 9D, the central longitudinal centerline X of the stent 50 may be offset from the line of intersection W of the first plane Y-Y' and the second plane Z-Z' and located in a fourth quadrant (quadrant IV) at a fourth cross-sectional location along the length of the stent 50 between the first and second ends.

Once the stent 50 has been deflected to a desired curved configuration, the stent 50 may be delivered into the gastrointestinal tract to be placed in a remaining portion of the stomach subsequent to a bariatric procedure. For example, FIG. 10A is a schematic illustration of the stent of FIG. 3 placed in a sleeve portion of a stomach following a gastric sleeve procedure. The curvature of the stent 50 may be selected to space the distal end of the stent 50 away from a tissue wall of the anatomical location in which the stent 50 is placed, such as spaced away from the inner wall of the remaining portion of the stomach (e.g., stomach sleeve) along the staple line 20, as shown in FIG. 10A, to reduce irritation of tissue along the stomach lining. FIG. 10B is a schematic illustration of the stent of FIG. 3 placed in a pouch portion of a stomach following a Roux-en-Y procedure. The curvature of the stent 50 may be selected to correspond to the curvature of the anatomical location in which the stent 50 is placed, such as along the remaining portion of the stomach (e.g., stomach pouch) and into the intestine, as shown in FIG. 10B, to reduce irritation of tissue along the gastrointestinal tract. In other instances, the stent 50 may be placed in the remaining portion of the stomach subsequent to a bariatric procedure, and then manipulated into a curved configuration in situ by pulling one or more drawstrings 80 while watching the curvature of the stent 50 under fluoroscopy, for example, until the stent 50 is in a desired curved configuration.

The stent 50 may include a locking mechanism 90 (shown generically in FIG. 3) proximate the proximal end 54 of the tubular framework 52 configured to hold the drawstring 80 in tension with the tubular framework 52 in the curved configuration. In other words, the drawstring 80 may be held in tension between the attachment location 84 and the locking mechanism 90 to hold the tubular framework 52, and thus the stent 50, in a desired curved configuration biased away from its natural straight configuration. In some instances, the locking mechanism 90 may be configured to allow the drawstring 80 to be pulled through the locking mechanism 90 in a first direction (i.e., a proximal direction opposite the attachment location 84), yet restrict or prevent the drawstring 80 to be pulled through the locking mechanism 90 in an opposite, second direction (i.e., in a distal direction toward the attachment location 84). In some instances, the locking mechanism 90 may be configured to selectively release the drawstring 80 to allow the drawstring 80 to be pulled back through the locking mechanism 90 in the second direction if it is desired to reduce the curvature placed on the stent 50 (i.e., increase the radius of curvature of the axial centerline X of the stent 50). Some exemplary locking mechanisms are illustrated in FIGS. 9-14B.

Figure 11:
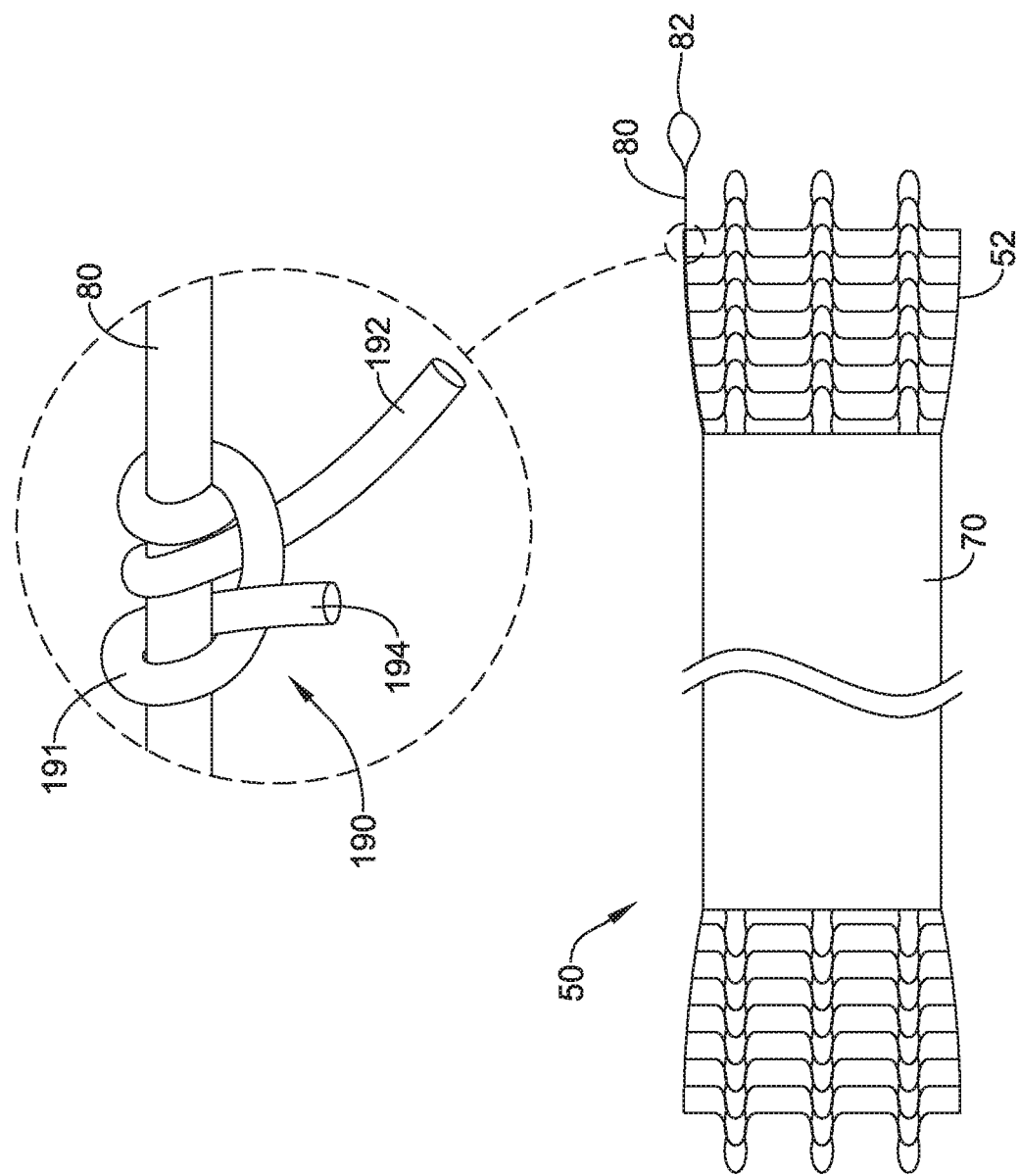
FIG. 11 illustrates an exemplary locking mechanism for retaining the drawstring of the stent of FIG. 3 in a tensioned state.
Figure 11A:
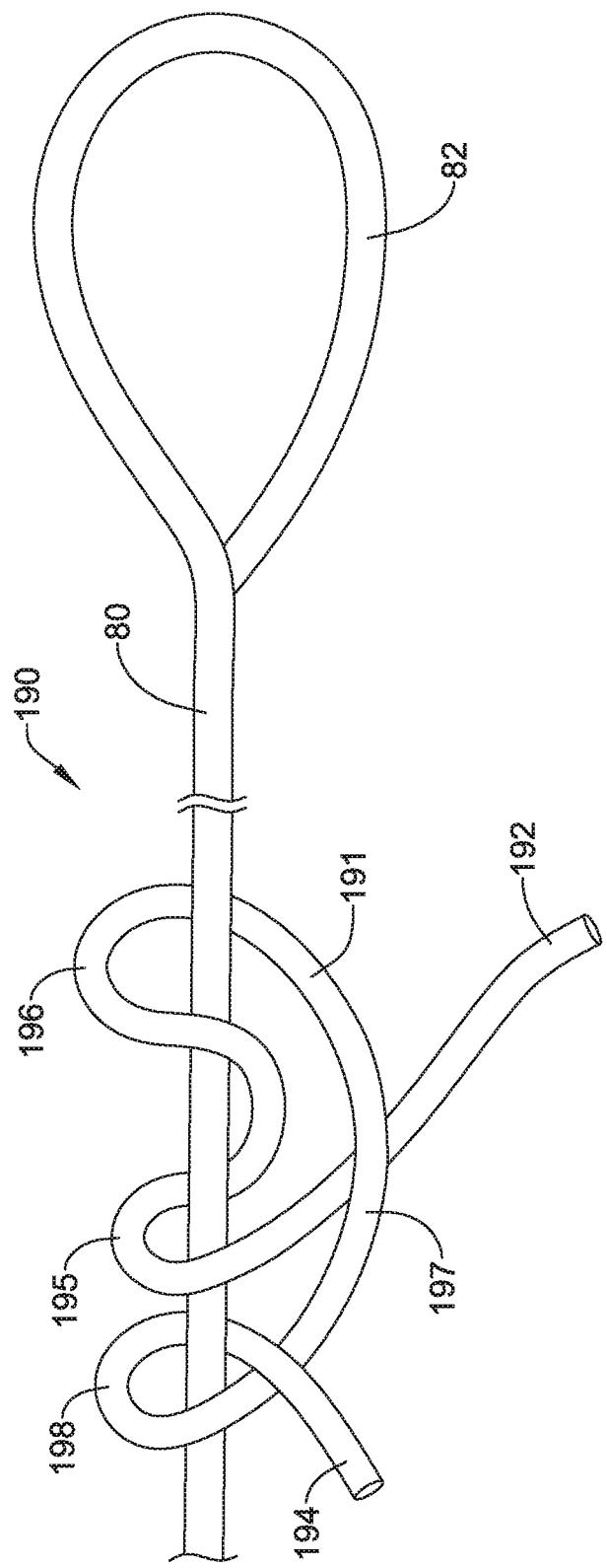
FIG. 11A illustrates formation of an exemplary hitch knot used as a locking mechanism described in association with FIG. 11.

FIG. 11 illustrates a first locking mechanism, shown as a knot, namely a hitch knot 190 formed by a filament 191. The drawstring 80 may extend through the hitch knot 190, with the filament 191 wrapped around the drawstring 80 multiple times. FIG. 11A illustrates how to tie the hitch knot 190 onto the drawstring 80. The filament 191 may be wrapped around the drawstring about two revolutions, forming the first winding 195 of the filament 191 and the second winding 196 of the filament 191. The second winding 196 may be located adjacent one side of the first winding 195. The segment 197 of the filament 191 extending from the second winding 196 may then cross over the first end region 192 of the filament 191 (i.e., the end region of the filament 191 extending from the first winding 195) and form a third winding 198 of the filament 191 around the drawstring 80 on the opposite side of the first winding 195 while passing the second end region 194 of the filament 191 between the segment 197 and the drawstring 80. Tightening the knot 190, shown in FIG. 11, cinches the knot 190 around the drawstring 80. The first end region 192 may then be tensioned and secured to the tubular framework 52. The applied tension on the drawstring 80 acts to tighten the knot 190 and cinch the first winding 195, the second winding 196, and the third winding 198 together and down on the drawstring 80. In some embodiments, the first and second end regions 192, 194 may then be secured to the tubular framework 52. In some instances, the first and second end regions 192, 194 may be tied to the tubular framework 52, such as threaded in and out of the tubular framework 52 and then tied together to secure the filament 191, and thus the hitch knot 190 to the tubular framework 52. In some instances, the end region 192 may be linked to one or more additional knots 190, thus anchoring one knot 190 to another knot 190 and securing the filament 191 to the tubular framework 52. In some instances, the filament 191 may be used to form one or more additional hitch knots 190 for one or more additional drawstrings 80, or an additional filament 191 may be used to form another hitch knot 190 for another drawstring 80 in instances in which the stent 50 includes multiple drawstrings 80. In some instances, the hitch knots 190 may be linked through interweaving the end region 192 between knots 190 through the tubular framework 52, thus creating an anchor from one knot 190 to another knot 190.

Another locking mechanism 290 is illustrated in FIG. 12. The locking mechanism 290 may include a grip sleeve 292 through which the drawstring 80 may extend. The grip sleeve 292 may be secured to the tubular framework 52 proximate the proximal end of the stent 50, for example. In some instances, the locking mechanism 290 may include a plurality of grip sleeves 292 attached together with a frame or collar 294. For instance, the frame or collar 294 may be an annular collar, shown in FIG. 12A, positioned within the lumen of the tubular framework 52 and contacting the inner surface of the tubular framework 52. As shown in FIG. 12A, a plurality of grip sleeves 292 may be symmetrically arranged around the annular collar 294, for example.

Figure 12B:
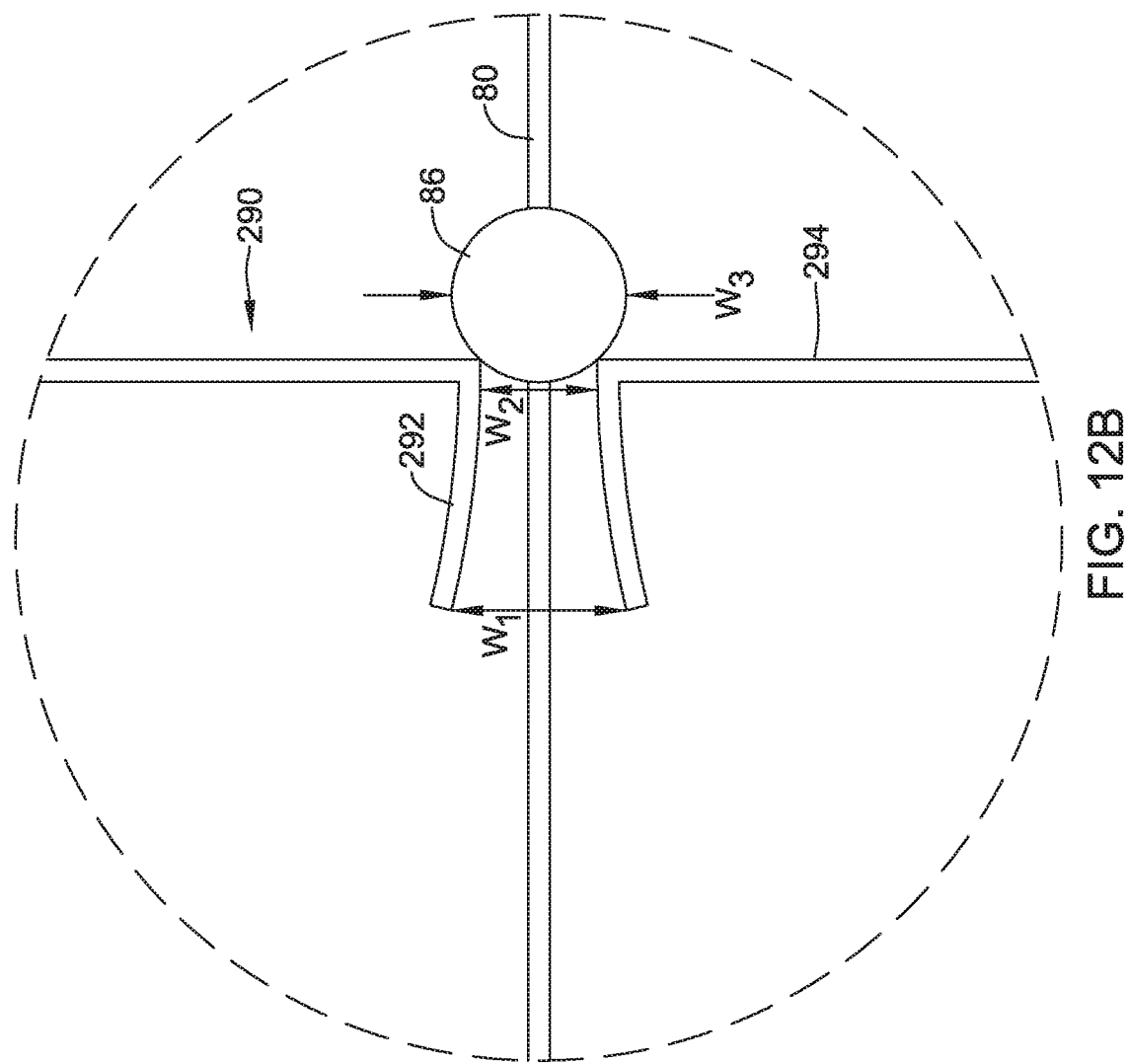
FIG. 12B is a longitudinal cross-sectional view taken through the locking mechanism of FIG. 12.

The grip sleeve 292 may be configured to allow the drawstring 80 to be pulled through the grip sleeve 292 in a first direction (i.e., a proximal direction opposite the distal end of the drawstring 80 and the attachment location 84), yet restrict or prevent the drawstring 80 to be pulled through the grip sleeve 292 in an opposite, second direction (i.e., in a distal direction toward the attachment location 84). For instance, as shown in FIG. 12B, the conically shaped grip sleeve 292 may include a lumen having distal opening having a width $W_1$ tapering down in a proximal direction to a width $W_2$. The drawstring 80 may include one or more, or a plurality of nodes 86 positioned along the drawstring 80. The nodes 86 may be enlarged protuberances arranged on the drawstring 80 having a width $W_3$. In some instances, the nodes 86 may be knots, beads or other enlarged structures positioned along the drawstring 80. The drawstring 80 may include a plurality of spaced apart nodes 86. The nodes 86 may be configured such that the width $W_3$ is less than the width $W_1$ at the distal end of the grip sleeve 292, but greater than the width $W_2$. Accordingly, the node 86 may be pulled through the lumen of the grip sleeve 292 in a distal-to-proximal direction, while prevented from being pulled back through the lumen of the grip sleeve 292 in a proximal-to-distal direction. The grip sleeve 292 may be flexible or deflectable such that the grip sleeve 292 is configured to radially expand and/or the node 86 may be sufficiently compressible as the node 86 passes through the lumen in the distal-to-proximal direction. The nodes 86 along the drawstring 80 may be sequentially pulled through the lumen of the grip sleeve 292 until the desired curvature of the stent 50 is achieved. Thereafter, the last node 86 passing through the grip sleeve 292 may abut the proximal opening of the grip sleeve 292 to retain tension in the drawstring 80.

In some instances, the grip sleeve 292 may be configured to selectively release the drawstring 80 to allow the drawstring 80 to be pulled back through the locking mechanism 290 in the second direction if it is desired to reduce the curvature placed on the stent 50 (i.e., increase the radius of curvature of the axial centerline X of the stent 50). For example, as shown in FIG. 12A, the grip sleeve 292 may include a slot 296 extending through a sidewall of the grip sleeve 292 into the lumen of the grip sleeve 292. The slot 296 may have a width $W_4$ greater than the width of the drawstring 80, but less than the width $W_3$ of the node 86, permitting the drawstring 80 to be moved laterally out of the lumen of the grip sleeve 292 through the slot 296 if desired. Once removed laterally from the grip sleeve 292, the drawstring 80 may be allowed to move distally relative to the locking mechanism 290.

Figure 13A:
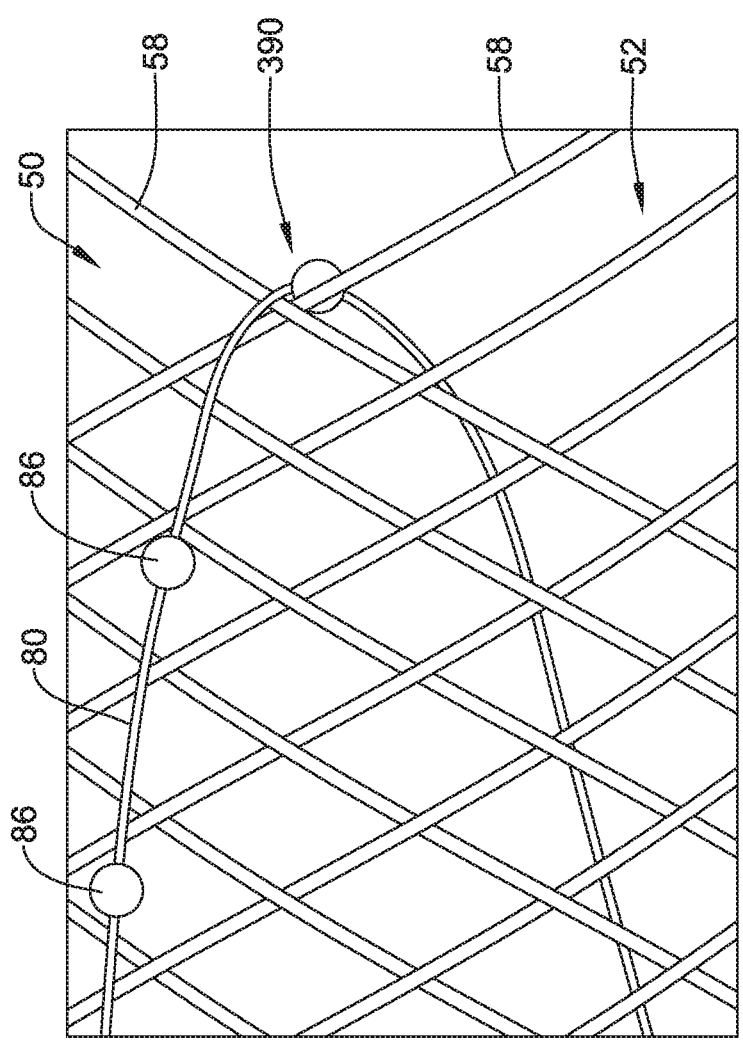
FIG. 13A is a side view illustrating an exemplary locking mechanism utilizing the structure of the tubular framework of the stent of FIG. 3.
Figure 13B:
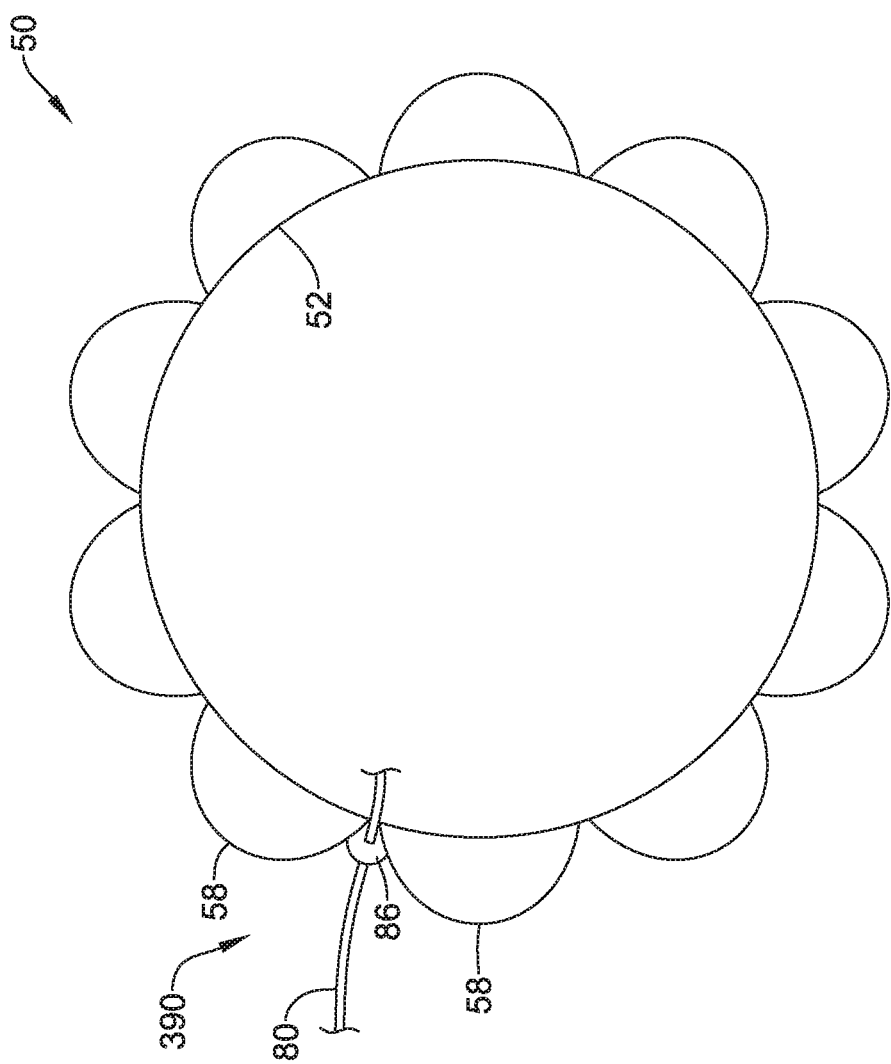
FIG. 13B is an end view illustrating an alternative locking mechanism utilizing the structure of the tubular framework of the stent of FIG. 3.

Another embodiment of a locking mechanism 390 utilizing one or more, or a plurality of nodes 86 positioned along the drawstring 80 is shown in FIGS. 13A-13B. As shown in FIG. 13A, the stent 50 may be configured such that a node 86 may engage one or more filaments 58 of the tubular framework 52 to secure the drawstring 80 in a tensioned state. For example, the drawstring 80 may pass across a V-shaped structure of the tubular framework 52 such that the node 86 engages in the base of the V-shaped structure. In some instances, the V-shaped structure may be formed at a location where filaments of the tubular framework 52 intersect, as shown in FIG. 13A. Alternatively, the V-shaped structure may be formed where end loops of the filaments of the tubular framework 52 converge at the proximal open end of the tubular framework 52 as shown in FIG. 13B.

Figure 14A:
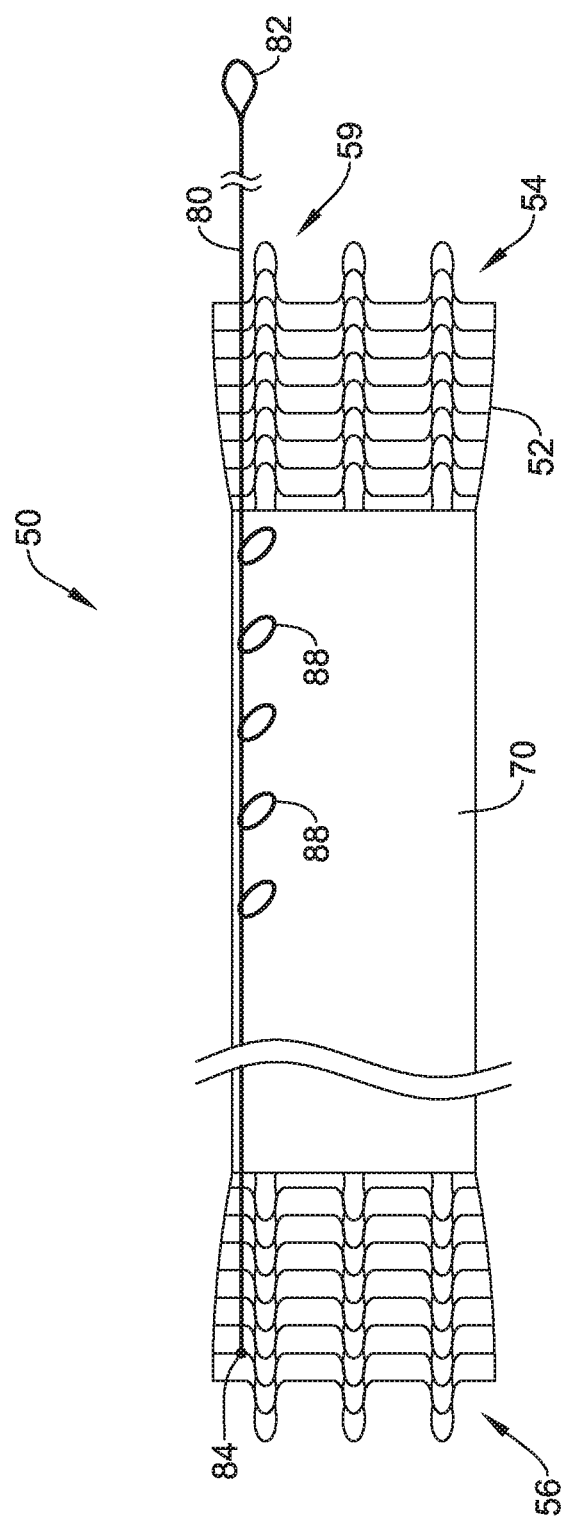
FIGS. 14A-14C illustrate aspects of an alternate configuration of a drawstring and locking structure of the stent of FIG. 3.
Figure 14B:
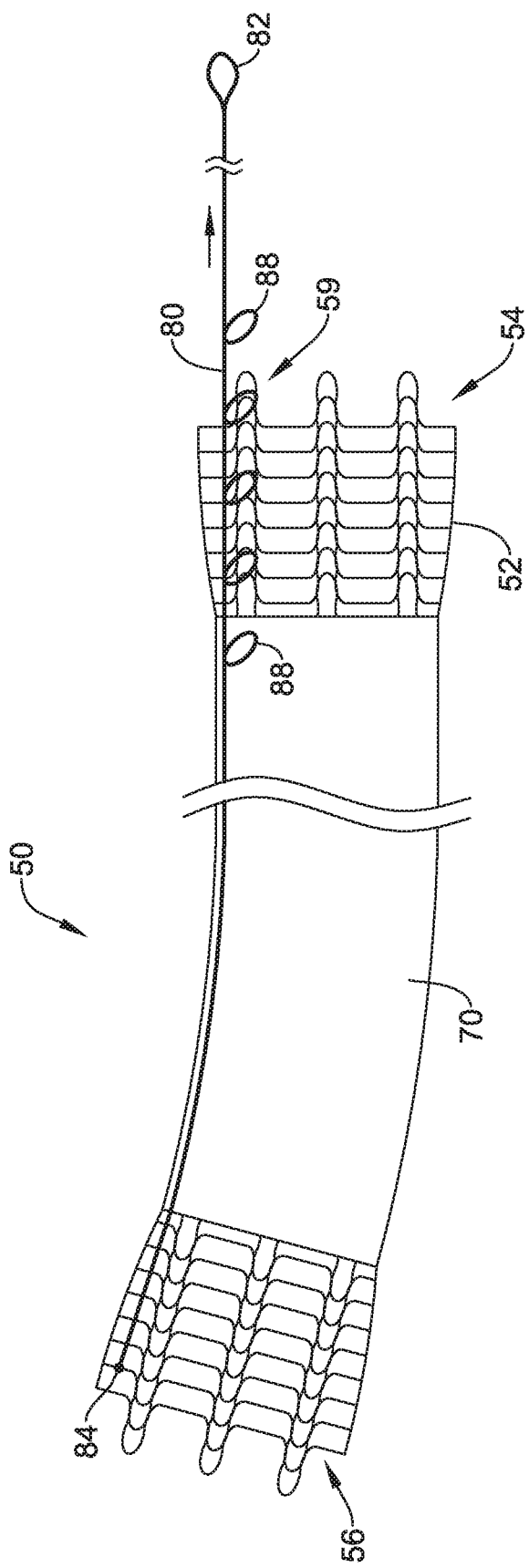
Figure 14C:
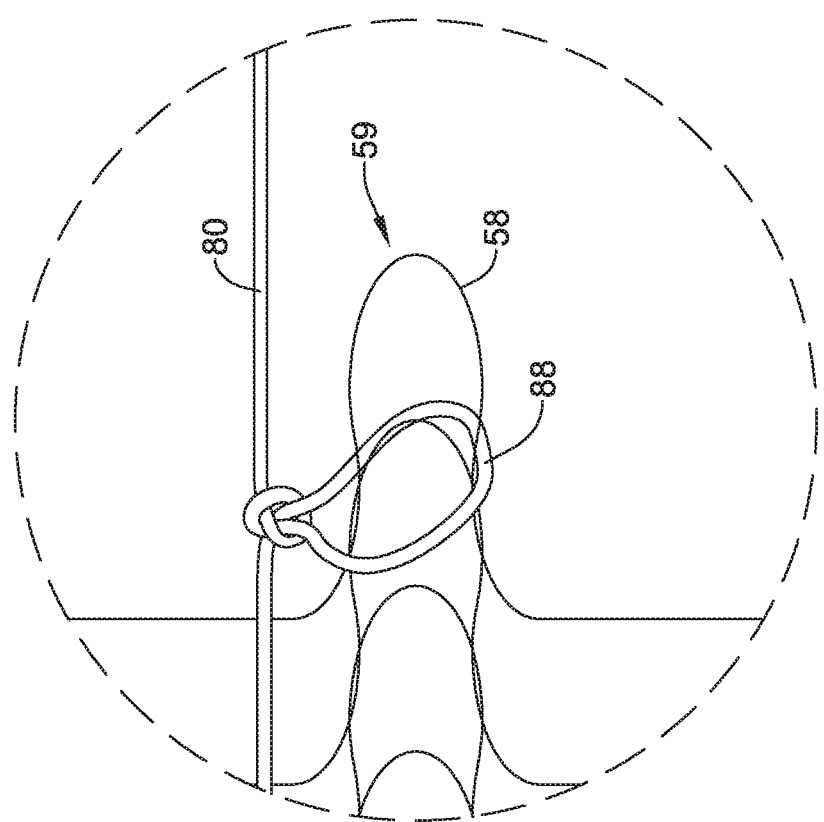

Another embodiment, shown in FIG. 14A, includes a locking mechanism utilizing one or more or a plurality of loops 88 formed along the drawstring 80. The loops 88 may be configured to be selectively looped around a structural component of the tubular framework 52, such as an end loop 59 formed by one or more of the filaments 58 of the tubular framework 52, as shown in FIG. 14C. Thus, the drawstring 80 may be pulled proximally until the tubular framework 52 is placed in a desired curved configuration, and then one of the loops 88 may be looped around the structural component (e.g., the end loop 59) of the tubular framework 52 to hold the drawstring 80 in tension and restrain the tubular framework 52 to the curved configuration, as shown in FIG. 14B. If it is desired to adjust the curvature, the loop 88 may be removed from the structural component (e.g., the end loop 59) of the tubular framework 52 and a loop 88 positioned at a different location along the drawstring 80 may be looped around the structural component (e.g., the end loop 59). If it is desired to allow the tubular framework 52 to revert back to its straight configuration, the loop 88 may be removed from the structural component (e.g., the end loop 59) of the tubular framework 52, thus removing the tension on the drawstring 80.

Another embodiment of a stent 450 configured to be selectively curved into a desired curved configuration is shown in FIGS. 15A and 15B. The stent 450 may be configured to be placed across the tissue walls T of two adjacent body lumens, connecting the two adjacent body lumens. Such a stent 450 may include a first flange 462 proximate a first end of the stent 450 and a second flange 464 proximate a second end of the stent 450. The flanges 462/464 may be configured to be placed against the luminal surface of the tissue walls T of the adjacent body lumens. In instances where the thickness of the tissue walls T is uniform, as shown in FIG. 15A, the stent 450 may be placed in its straight configuration. However, in instances where the thickness of the tissue walls T is not uniform, as shown in FIG. 15B, the stent 450 may be placed in a curved configuration to draw the flanges 462, 464 nearer together on one side of the stent 450 to bring the flanges 462, 464 against the tissue wall while accommodating the thicker tissue wall on the opposite side of the stent 450. For example, the stent 450 may include a drawstring 480 attached to the tubular framework 452 of the stent 450 at an attachment location 484 proximate the second flange 484 at one end of the stent 450. The drawstring 480 may include a loop 488 that can be selectively looped onto a locking structure 486, such as a hook, etc. proximate the first flange 482 at the other end of the stent 450 to hold the drawstring 480 in tension with a desired curvature in the stent 450. Alternatively, the drawstring 480 may be secured at opposing ends of the stent 450, with a slidable knot formed in the drawstring 480 at an intermediate location. The slidable knot may be moved along the drawstring 480 to adjust the tensioned length of the drawstring 480 between the securement locations to therefore hold the stent 450 in a desired curved configuration.

Figure 16A:
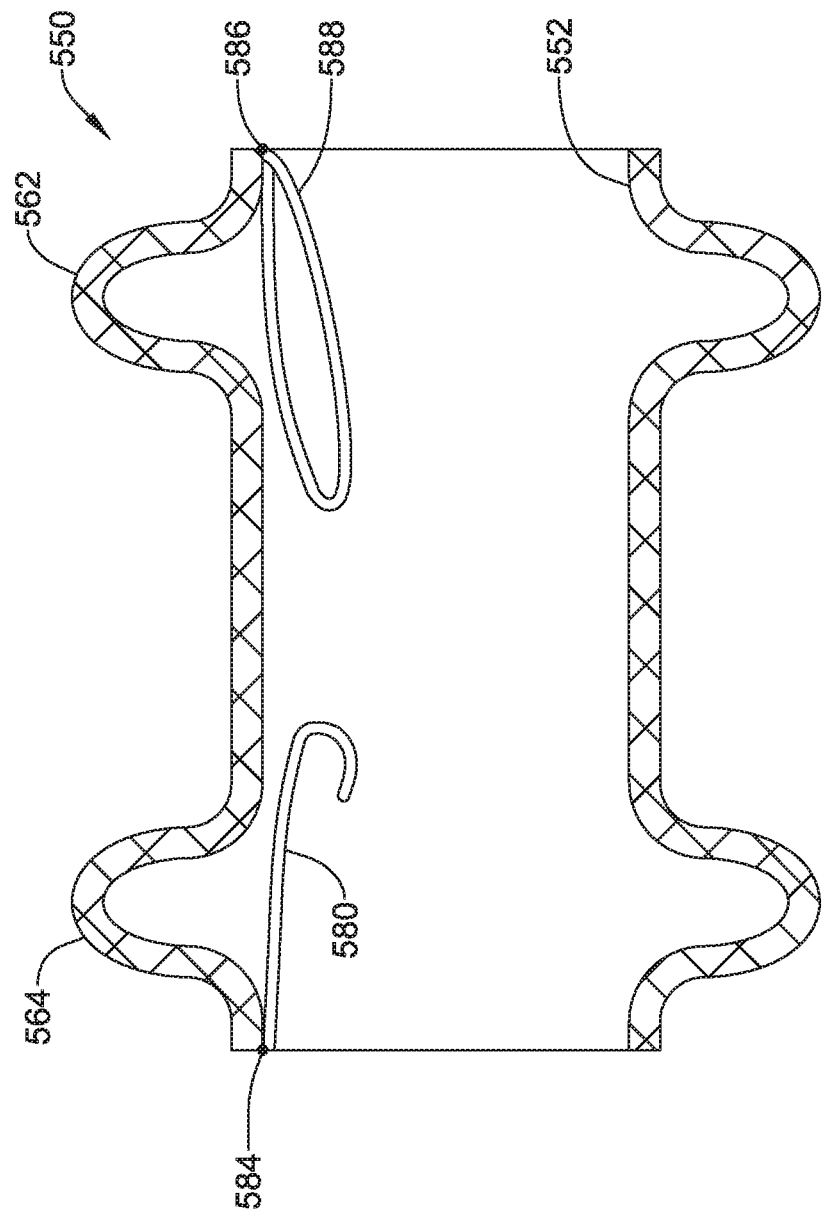
FIGS. 16A and 16B illustrate aspects of another alternative stent configured to connect luminal passages of adjacent body lumens.
Figure 16B:
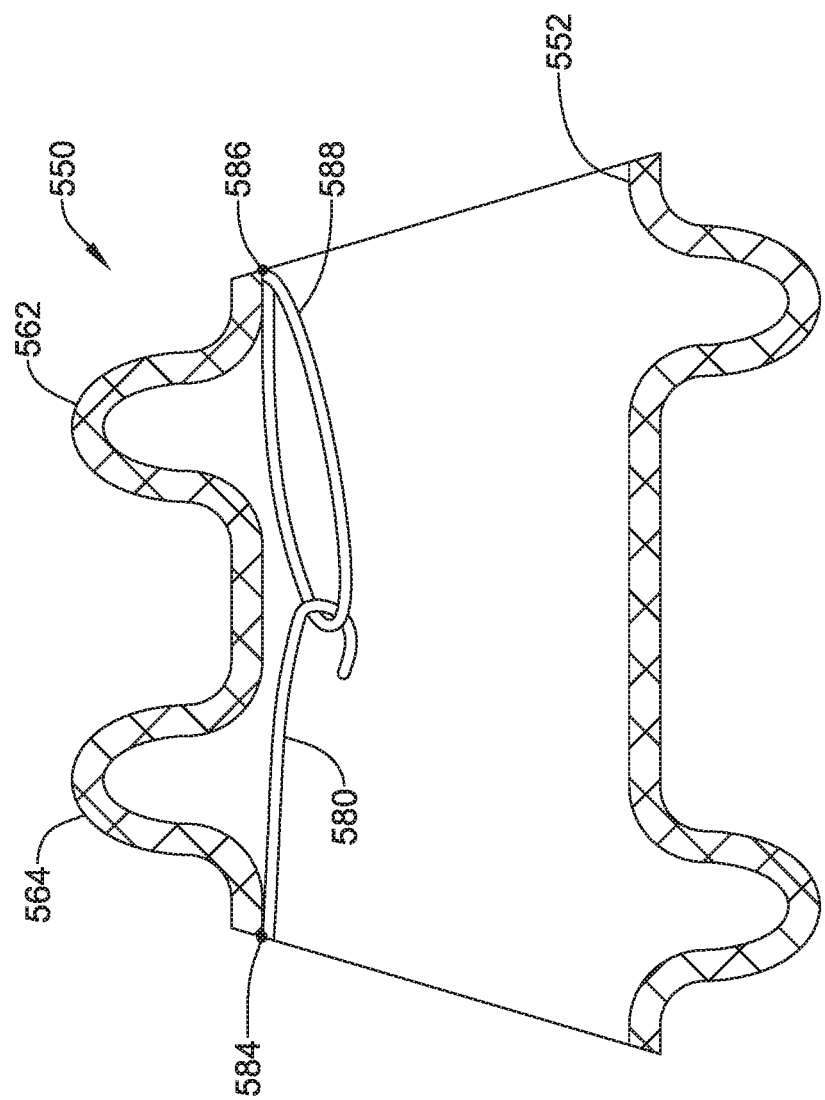

Another embodiment of a stent 550 configured to be selectively curved into a desired curved configuration is shown in FIGS. 16A and 16B. Similar to the stent 450, the stent 550 may be configured to be placed across the tissue walls of two adjacent body lumens, connecting the two adjacent body lumens. The stent 550 may include a first flange 562 proximate a first end of the stent 550 and a second flange 564 proximate a second end of the stent 550. The flanges 562/564 may be configured to be placed against the luminal surface of the tissue walls of the adjacent body lumens. In instances where the thickness of the tissue walls is uniform, the stent 550 may be placed in its straight configuration, as shown in FIG. 16A. However, in instances where the thickness of the tissue walls is not uniform, the stent 550 may be placed in a curved configuration to draw the flanges 562, 564 nearer together on one side of the stent 550 to bring the flanges 562, 564 against the tissue wall while accommodating the thicker tissue wall on the opposite side of the stent 550, as shown in FIG. 16B. For example, the stent 550 may include a hook 580 attached to the tubular framework 552 of the stent 550 at an attachment location 584 proximate the second flange 584 at one end of the stent 550. The hook 580 may be selectively hooked onto a loop 588 attached to the tubular framework 552 of the stent 550 at an attachment location 586 proximate the first flange 582 at the other end of the stent 550 to hold the stent 550 in a desired curved configuration. The loop 588 may be a portion of the tubular framework 552 or a separate structure secured to the tubular framework 552, for example. In some instances, the stent 550 may include a plurality of loops 588 at longitudinal spaced apart locations to selectively hold the stent 550 in one of a plurality of curved configuration depending upon which loop 588 the hook 580 is hooked onto.

It is noted that in many of the embodiments described herein, the drawstring is tensioned between two points proximate the ends of the stent. However, in other embodiments, the drawstring may be secured at a first attachment point located at any desired location along the length of the stent, and then pulled into tension and secured at a second attachment point spaced away from the first attachment point and located at any other desired location along the length of the stent. For example, the locking mechanism (e.g., hitch knot, grip sleeve, etc.) may be located at any location along the stent, with the drawstring tensioned between the attachment location at the distal end of the drawstring and the locking mechanism. Thus, the stent may be placed into a curved configuration between the attachment location and the locking mechanism, while portions of the stent extending beyond the attachment location and the locking mechanism may remain in a straight configuration.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A stent comprising:
 a radially expandable tubular framework having a proximal end, a distal end, and a lumen extending therethrough along a central longitudinal centerline;
 a covering surrounding the tubular framework;
 a first drawstring having a first end and a second end, the first end of the first drawstring attached to the tubular framework at a first attachment location proximate the distal end of the tubular framework; and
 a second drawstring having a first end and a second end, the first end of the second drawstring attached to the tubular framework at a second attachment location proximate the distal end of the tubular framework, the second attachment location being circumferentially spaced apart from the first attachment location around a circumference of the tubular framework;
 wherein the second end of the first drawstring and the second end of the second drawstring are configured to be pulled proximate the proximal end of the tubular framework to deflect the tubular framework to move the central longitudinal centerline of the tubular framework into a compound curved configuration.

2. The stent of claim 1, wherein the first drawstring extends along the tubular framework between an inner surface of the covering and an outer surface of the tubular framework.

3. The stent of claim 2, wherein:
 a distal end region of the covering is affixed to the tubular framework at a first affixment location;
 a proximal end region of the covering is affixed to the tubular framework at a second affixment location;
 wherein the second affixment location is spaced proximally away from the first affixment location; and
 wherein the covering surrounds but is not directly affixed to the tubular framework between the first affixment location and the second affixment location.

4. The stent of claim 3, wherein the first drawstring passes radially inward of the first affixment location as the first drawstring passes distally from the first affixment location to the attachment location.

5. The stent of claim 4, wherein the first drawstring passes radially inward of the second affixment location as the first drawstring passes proximally from the second affixment location to the proximal end of the tubular framework.

6. The stent of claim 1, further comprising a third drawstring having a first end and a second end, the first end of the third drawstring attached to the tubular framework at a third attachment location proximate the distal end of the tubular framework, the third attachment location being circumferentially spaced apart from the first and second attachment locations around the circumference of the tubular framework.

7. The stent of claim 6, wherein the first, second and third attachment locations are spaced about 120° apart about the circumference of the tubular framework.

8. The stent of claim 6, further comprising a fourth drawstring having a first end and a second end, the first end of the fourth drawstring attached to the tubular framework at a fourth attachment location proximate the distal end of the tubular framework, the fourth attachment location being circumferentially spaced apart from the first, second and third attachment locations around the circumference of the tubular framework.

9. The stent of claim 8, wherein the first, second, third and fourth attachment locations are spaced about 90° apart about the circumference of the tubular framework.

10. The stent of claim 1, further comprising a locking mechanism proximate the proximal end of the tubular framework, the locking mechanism configured to hold the first drawstring in tension with the tubular framework in the curved configuration.

11. The stent of claim 10, wherein the locking mechanism includes a filament wrapped around the first drawstring to form a hitch knot.

12. The stent of claim 11, wherein the first drawstring is movable through the hitch knot in a proximal direction, but the hitch knot prevents the first drawstring from moving through the hitch knot in a distal direction.

13. The stent of claim 10, wherein the first drawstring includes either:
 one or more nodes positioned along a length of the first drawstring, wherein the one or more nodes are configured to selectively engage the locking mechanism; or
 one or more loops positioned along a length of the first drawstring, wherein the one or more loops are configured to selectively engage the locking mechanism.

14. A stent comprising:
 a radially expandable tubular framework having a proximal end, a distal end, and a lumen extending therethrough along a central longitudinal centerline, the tubular framework formed of one or more filaments;
 a covering surrounding a medial region of the tubular framework such that a proximal end region of the tubular framework extends proximal of the covering and is devoid of any covering, and a distal end region of the tubular framework extend distal of the covering and is devoid of any covering; and
 a drawstring having a first end secured to the one or more filaments of the tubular framework at a first attachment location, wherein the drawstring extends along the tubular framework between an inner surface of the covering and an outer surface of the tubular framework;
 wherein a second end of the drawstring is configured to be pulled proximate the proximal end of the tubular framework to deflect the tubular framework to move the central longitudinal centerline of the tubular framework into a curved configuration.

15. The stent of claim 14, further comprising a filament wrapped around the drawstring to form a hitch knot, wherein the drawstring is movable through the hitch knot in a proximal direction, but the hitch knot prevents the drawstring from moving through the hitch knot in a distal direction.

16. The stent of claim 14, wherein the drawstring includes a plurality of nodes positioned along a length of the drawstring, wherein the plurality of nodes are configured to selectively engage a locking mechanism to retain the tubular framework in the curved configuration.

17. The stent of claim 14, wherein the drawstring includes a plurality of loops positioned along a length of the drawstring, wherein the plurality of loops are configured to selectively engage a locking mechanism to retain the tubular framework in the curved configuration.

18. A method of implanting a stent into a gastrointestinal tract in which only a portion of the stomach remains of a patient subsequent a bariatric surgical procedure, the method comprising:
pulling a drawstring of a stent to deflect a tubular framework of the stent into a curved configuration such that a central longitudinal centerline of the stent extends in an arcuate path;
securing the drawstring to the stent with the drawstring held in tension to maintain the curved configuration; and
positioning the stent into the remaining stomach portion of the patient with the tubular framework in the curved configuration.

* * * * *